United States Patent
Neiss et al.

(10) Patent No.: US 7,532,320 B2
(45) Date of Patent: May 12, 2009

(54) MULTIMODAL METHOD FOR IDENTIFYING HAZARDOUS AGENTS

(75) Inventors: Jason Neiss, Pittsburgh, PA (US); Matthew P. Nelson, Harrison City, PA (US); Patrick Treado, Pittsburgh, PA (US); Robert Schweitzer, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 383 days.

(21) Appl. No.: 11/000,841

(22) Filed: Nov. 30, 2004

(65) Prior Publication Data

US 2008/0192246 A1 Aug. 14, 2008

Related U.S. Application Data

(60) Provisional application No. 60/591,132, filed on Jul. 26, 2004, provisional application No. 60/584,719, filed on Jun. 30, 2004.

(51) Int. Cl.
*G01J 3/44* (2006.01)
(52) U.S. Cl. .............................. 356/301; 356/72; 356/73
(58) Field of Classification Search .................. 356/72, 356/73, 301
See application file for complete search history.

(56) References Cited

U.S. PATENT DOCUMENTS

| | | | |
|---|---|---|---|
| 5,442,438 A | 8/1995 | Batchelder et al. | |
| 5,638,166 A | 6/1997 | Funsten et al. | |
| 5,759,859 A | 6/1998 | Sausa | |
| 5,866,430 A * | 2/1999 | Grow | 436/172 |
| 6,002,476 A * | 12/1999 | Treado | 356/301 |
| 6,174,732 B1 * | 1/2001 | Ong et al. | 436/177 |
| 6,734,962 B2 * | 5/2004 | Treado et al. | 356/301 |
| 6,954,667 B2 * | 10/2005 | Treado et al. | 600/476 |
| 7,088,435 B2 * | 8/2006 | Brestel et al. | 356/72 |
| 7,092,101 B2 * | 8/2006 | Brady et al. | 356/456 |
| 7,108,970 B2 * | 9/2006 | Levinson | 435/6 |
| 7,123,359 B2 * | 10/2006 | Armstrong et al. | 356/301 |
| 2005/0185178 A1 * | 8/2005 | Gardner et al. | 356/301 |

OTHER PUBLICATIONS

Pinnick et al., 1999, Field Anal. Chem. Technol. 3:221-239.

* cited by examiner

*Primary Examiner*—Tarifur Chowdhury
*Assistant Examiner*—Jonathon D Cook
(74) *Attorney, Agent, or Firm*—Morgan Lewis & Bockius LLP

(57) ABSTRACT

The invention relates to apparatus and methods for assessing occurrence of a hazardous agent in a sample by performing multimodal spectral analysis of the sample. Methods of employing Raman spectroscopy for entities in a sample which exhibit one or more optical properties characteristic of a hazardous agent are disclosed. Devices and systems suitable for performing such methods are also disclosed.

35 Claims, 22 Drawing Sheets
(4 of 22 Drawing Sheet(s) Filed in Color)

FIG. 4A

MULTIMODAL METHOD FOR IDENTIFYING HAZARDOUS AGENTS

CROSS-REFERENCES TO RELATED APPLICATIONS

This application is entitled to priority pursuant to 35 U.S.C. § 119(e) to U.S. provisional patent application 60/584,719, which was filed on 30 Jun. 2004, as well as to U.S. provisional patent application 60/591,132, which was filed on 26 Jul. 2004. Each of said provisional patent applications is incorporated herein in its entirety.

BACKGROUND OF THE INVENTION

The invention relates generally to the field of Raman spectroscopy.

Deliberate and inadvertent deployments of harmful or weaponized chemical or biological agents pose significant threats to public welfare, as do explosives and radiological materials. Such agents threaten both human and economic health, and the threats posed by these agents are compounded by limited ability to detect deployment of the agents and to respond appropriately.

The mass destruction potential of biological weapon agents (BWAs) and chemical weapon agents (CWAs) is considered comparable to or even greater than that of nuclear weapons. Nuclear weapons have the potential to affect a finite area, albeit very large, and the use of such weapons is immediately obvious after the fact. The geographical site and boundaries of attacks using BWAs and CWAs are not readily apparent, and can be difficult to identify in a period of time relevant to permit effective response. Once unleashed, these agents can spread silently and unchecked through populations far from ground zero. Technology to rapidly detect and quantify radiation, even at very low levels, is widely available. Unfortunately, such technology for BWAs and CWAs at similar levels is not definitive, not widely available and in many cases, is not very rapid. A significant need exists for apparatus and methods useful for detecting and quantifying BWAs and CWAs in a timely manner.

Conventional means of identifying biological pathogens include methods and reagents such as specific antibodies, genetic markers, and propagation in culture. Most of these methods are slow, labor-intensive, and dependent on detection of highly-specific molecular structures. Using modern biotechnology methods, it is possible to alter many human pathogens in ways that can limit traditional detection methods, increase their pathogenicity, increase their resistance to conventional therapy, or some combination of these. Engineered BWAs pose a greater threat as biotechnology information becomes more widely available. Conventional tools for detecting BWAs are likely to become less effective over time as such knowledge spreads.

As unintended or deliberate use of BWAs and CWAs becomes a greater threat, there is an increased need for tools that can rapidly and accurately detect and classify these agents at a molecular level, preferably without coming into contact with them. These tools are also needed to help expand our understanding of the biological and chemical nature of such agents and their potential impact on the human body. The present invention satisfies these needs.

BRIEF SUMMARY OF THE INVENTION

The invention relates to a method of assessing occurrence of a hazardous agent in a sample, such as one that comprises multiple entities. The method comprises assessing a first optical property of the entities to select an entity for which the first optical property (e.g., absorbance, fluorescence, diffraction, polarization, or microscopic morphology) is characteristic of the hazardous agent. Raman-shifted radiation scattered by the selected entity is thereafter assessed. Exhibition of a Raman scattering property characteristic of the hazardous agent by the selected entity is indicative that the hazardous agent occurs in the sample. In one embodiment, Raman-shifted radiation scattered by a selected entity is assessed only if the selected entity also exhibits a second optical property characteristic of the hazardous agent.

By way of example, entities in a sample can be assessed to determine whether they exhibit a microscopic morphology and a fluorescent property characteristic of the hazardous agent. In order to speed the process, fluorescent properties can be assessed only for those entities which exhibit microscopic morphology characteristic of the hazardous agent (e.g., only for entities which exhibit the characteristic shape of a pathogenic bacterium). Entities that exhibit both characteristic properties can be selected for Raman scattering analysis, thereby reducing the amount of time spent on the more definitive, but typically less sensitive, Raman analysis.

The methods described herein are useful for assessing occurrence of a wide variety of hazardous agents. Examples of such agents include synthetic organic chemicals, biological toxins, microorganisms (e.g., bacteria and protozoa), and viruses.

The method can be performed using a variety of Raman-shifted scattered radiation collection systems. Such systems can be based on devices such as macroscopes, microscopes, endoscopes, and fiber optic arrays. The invention includes such devices and systems.

BRIEF SUMMARY OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 4 consists of FIGS. 4A and 4B. FIG. 4A is a graph of the Raman spectra of three *Bacillus* species and dipicolinic acid.

FIG. 5 consists of FIGS. 5A, 5B, 5C, and 5D. In FIG. 5A, "S1" is a Raman spectrum for *Bacillus globigii*, corresponding to entities designated "1" in FIGS. 5B and 5C; "S2" is a Raman spectrum for egg white, corresponding to entities designated "2" in FIG. 5B; and "S3" is a Raman spectrum for *Aspergillus terreus* spores, corresponding to the entity designated "3" in FIGS. 5B and 5D.

FIG. 6, consisting of FIGS. 6A, 6B, and 6C, depicts fluorescence spectral differentiation and identification of different *Bacillus* species in a mixture of *B. pumilus* and *B. subtilis*.

FIG. 8, consisting of FIGS. 8A, 8B, 8C, and 8D, depicts use of fluorescence sensing performed on a commercial macro platform (CONDOR™ macro imaging system, ChemImage Corp., Pittsburgh, Pa.) for detecting spores of *B. globigii* mixed with baking soda on the exterior of an envelope.

DETAILED DESCRIPTION OF THE INVENTION

Figure 1:
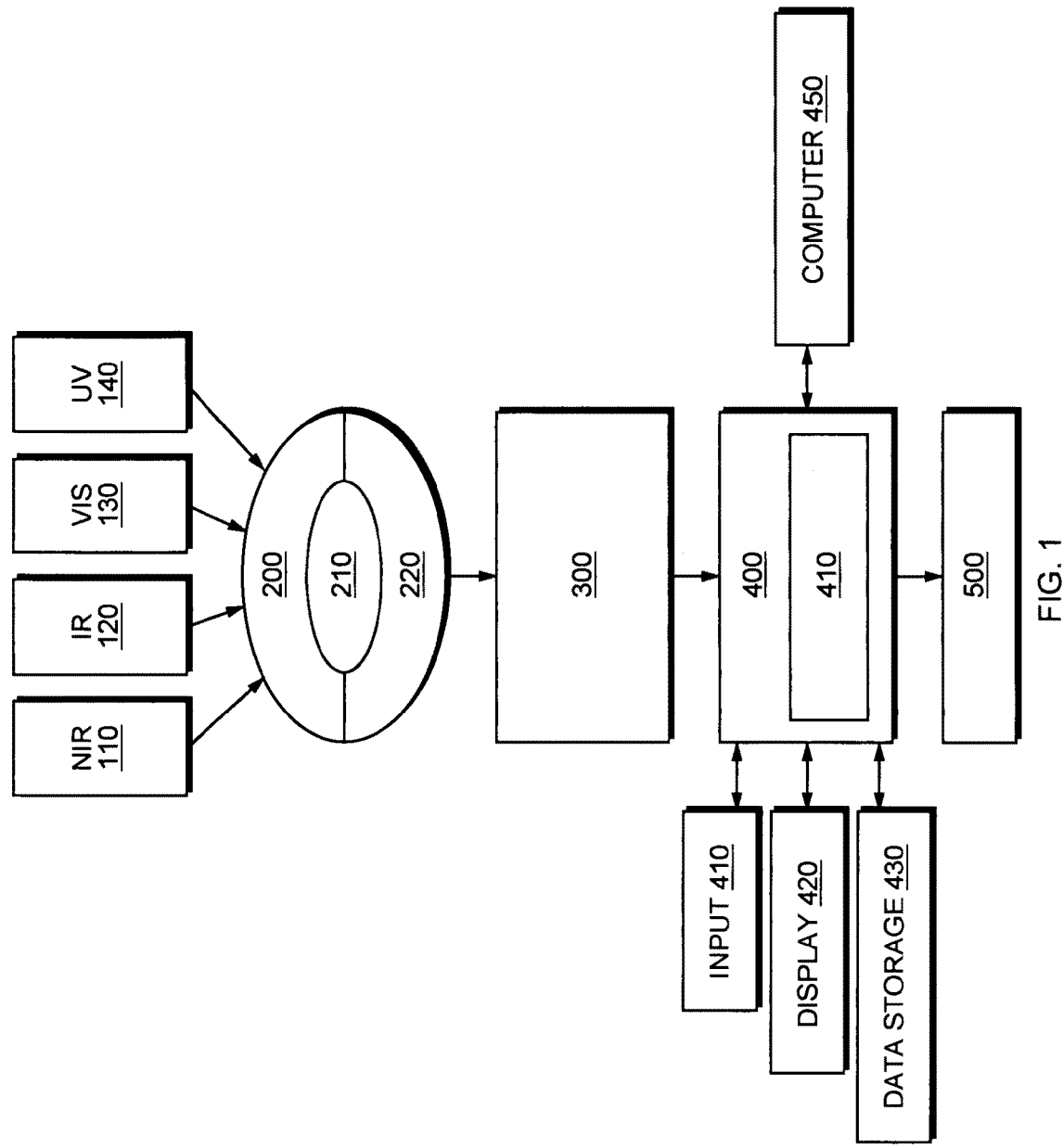
FIG. 1 is a schematic diagram of an instrument (or multiple configured instruments) suitable for use in the multimodal sensing and detection systems described herein.

The invention relates to a method of assessing occurrence of a hazardous agent in a sample, particularly when the sample contains multiple entities (e.g., debris, soot, dust, non-pathogenic microorganisms, and animal dander) other than the hazardous agent. Samples collected from various environments (e.g., ambient indoor and outdoor air samples, soil samples, and unknown powders) often include particulate entities which have certain properties in common with hazardous agents, and identifying and/or quantifying the hazardous agents in the sample milieu can be significantly complicated and slowed by the apparent similarity of the entities in the sample. In situations in which rapid detection of hazardous agents is desired, traditional rapid microscopic and fluorescent analytical methods often exhibit insufficient sensitivity to positively identify hazardous agents and differentiate them from other entities.

Raman spectroscopy can be used to assess the Raman scattering properties of all entities in the sample to identify entities which exhibit Raman scattering properties that are characteristic of the hazardous agent. In view of the amount and type of information that can be discerned from Raman scattering properties, those properties can often be highly informative for identifying hazardous agents in a sample. However, owing to a number of factors (e.g., relatively weak signal strength, frequent occurrence of background fluorescence, and relatively slow operation of Raman scattering analytical equipment), the time required for obtaining informative Raman scattering information for all candidate entities in a sample can exceed the time available or convenient for sample analysis, particularly when rapid analysis is necessary.

The methods described herein permit more rapid Raman scattering analysis of potential hazardous agents in a sample by using more rapid optical analytical methods (e.g., microscopic and/or fluorescent analysis) to exclude from Raman scattering analysis entities that do not exhibit optical characteristics characteristic of a hazardous agent.

The methods described herein comprise assessing a first optical property of the entities in the sample. Entities for which the first optical property is characteristic of the hazardous agent (i.e., consistent with the entity being the agent) can thereby be selected. Raman-shifted radiation scattered by one or more of those selected entities can thereafter be assessed. Entities for which the first optical property is not characteristic of the hazardous agent can be excluded from the Raman scattering analysis, thereby avoiding spending the time and computing resources that would otherwise be spent performing Raman scattering analysis of those non-characteristic entities. Occurrence in the sample of entities which exhibit both the first optical property and a Raman scattering property characteristic of the hazardous agent indicates that the sample comprises the hazardous agent.

In one embodiment, at least two optical properties of entities in the sample are assessed prior to Raman scattering analysis, and that analysis is performed only for entities for which each of the optical properties is characteristic of the hazardous agent. When two or more optical properties are assessed prior to Raman scattering analysis, failure of an entity to exhibit any of the optical properties characteristic of the hazardous agent can exclude that entity from Raman scattering analysis. Thus, failure of an entity to exhibit a first optical property characteristic of the hazardous agent makes it unnecessary to analyze that entity for a second or subsequent optical property. To the extent assessment of the second or subsequent optical property requires additional assay or processing time, the speed of the entire process can be increased by excluding entities which fail to exhibit even a single optical property of the hazardous agent from further analysis. Alternatively, two or more optical properties of entities in a sample can be assessed, and Raman scattering analysis can be performed for each entity that exhibits at least one optical property characteristic of the hazardous agent.

DEFINITIONS

As used herein, each of the following terms has the meaning associated with it in this section.

"Bandwidth" means the range of wavelengths in a beam of radiation, as assessed using the full width at half maximum method.

"Bandpass" of a detector or other system means the range of wavelengths that the detector or system can distinguish, as assessed using the full width at half maximum intensity method.

The "full width at half maximum" ("FWHM") method is a way of characterizing radiation including a range of wavelengths by identifying the range of contiguous wavelengths over which the magnitude of a property (e.g., intensity or detection capacity) is equal to at least half the maximum magnitude of that property in the radiation at a single wavelength.

A "hazardous agent" is a substance (e.g., a chemical, biological, radiological, or explosive material) that can cause disease, injury, discomfort, pain, or death to an animal such as a human.

"Spectral resolution" means the ability of a radiation detection system to resolve two spectral peaks.

The terms "optical" and "spectroscopic" are used interchangeably herein to refer to properties of materials (and to methods of assessing such properties). The term "spectroscopic" is generally understood to refer to the interaction of electromagnetic radiation, electrons, or neutrons with the materials. The term "optical" typically refers to an interaction with electromagnetic radiation. For example, although electron microscopy is not always commonly considered a "spectroscopic" or "optical" method, the two terms are used inclusively herein to encompass electron microscopy and other methods of assessing interaction of a material with visible, ultraviolet, or infrared light, with neutrons, or with other radiation.

DETAILED DESCRIPTION

The methods described herein comprise assessing a first optical property of the entities in a sample. Entities for which the first optical property is characteristic of a hazardous agent (i.e., consistent with the entity being the hazardous agent) are selected. Raman-shifted radiation scattered by one or more of those selected entities is thereafter assessed. Entities for which the first optical property is not characteristic of the hazardous agent can be excluded from the Raman scattering analysis, thereby avoiding spending the time that would otherwise be spent performing Raman scattering analysis of those non-characteristic entities. Occurrence in the sample of entities which exhibit both the first optical property and a Raman scattering property characteristic of the hazardous agent indicates that the sample comprises the agent.

At least a second optical property of the entities in the sample can be assessed. Those entities which fail to exhibit either of the first and second optical properties characteristic of the hazardous agent need not be assessed for Raman scattering. Excluding entities that fail to exhibit a rapidly-assessed optical property of the hazardous agent can reduce the amount of time spent performing Raman scattering analysis of entities that are not hazardous agents, thereby increasing the overall rapidity (i.e., throughput) of the assay method. Three, four, five, or more optical properties of entities in the sample can be assessed to select entities suitable for Raman scattering analysis, but such additional assessment can increase the complexity, cost, and computing power requirements of the system. One and two optical properties are considered sufficient discriminators for most purposes.

In one embodiment, a microscopic method is used to assess the morphology (i.e., size, shape, arrangement, or some combination of these) of entities in the sample. Entities having a morphology characteristic of the hazardous agent (e.g., the shape or chain configuration of a pathogenic bacterium) are selected for further analysis. Entities which exhibit a morphology consistent with the hazardous agent are assessed by fluorescence spectroscopy or fluorescence microscopy. Entities which exhibit fluorescence characteristic (i.e., exhibiting a characteristic wavelength(s), intensity, or delay of fluorescent or phosphorescent emission) of the hazardous agent are selected for Raman scattering analysis, and those entities which do not exhibit fluorescence characteristic of the hazardous agent are not analyzed further. Raman scattering analysis is thus performed only for entities which exhibit both the morphology and fluorescence characteristic of the hazardous agent. Exhibition of a Raman scattering property characteristic of the hazardous agent (e.g., one or both of a characteristic Raman shift and a characteristic Raman spectrum) is an indication that the entity is or comprises the agent. Using this method, occurrence of the hazardous agent in the sample can be detected in a rapid manner. This embodiment is depicted in a flow chart in FIG. 3.

In an alternative embodiment, a fluorescent microscopic or spectroscopic method can be used to select candidate entities for further microscopic morphological analysis. Entities in a sample which exhibit both the fluorescent and morphological characteristics of a hazardous agent of interest can be selected for Raman scattering analysis.

The order in which the optical analytical methods described herein are performed is not critical. However, in order to reduce the time necessary for Raman scattering analysis, at least part of that analysis should occur after entities in the sample have been assessed by another, more rapid analytical method (e.g., microscopic morphological analysis and/or fluorescent analysis) and confirmed to exhibit an optical property consistent with the optical properties of the hazardous agent. For example, optical analytical methods can be performed sequentially (e.g., first assessing microscopic morphology of all entities in a microscopic field including the sample, thereafter assessing fluorescent emissions from all entities in the field, and thereafter assessing Raman scattering from the entities in the field that exhibit morphological and/or fluorescent characteristics of the hazardous agent). Optionally, two or more of the analytical methods can be performed in parallel (e.g., microscopic morphology and fluorescent emissions can be assessed simultaneously for entities in a microscopic field), and Raman scattering analysis of selected entities can be performed thereafter, for example using multiple detectors suitable for collecting information simultaneously from the sample. Combined serial and parallel operations can be performed as well, in order to improve the speed of the method.

The methods described herein overcome shortcomings of single-mode analytical methods of the prior art. Techniques that rely on a single optical detection strategy can exhibit a high rate of false positive detection results. The frequency of such false positive results can vary widely depending on the material being analyzed. Attempts by others to overcome such shortcomings have tended to address individual shortcomings in the sensitivity of the individual methods used or specific limitations of particular optical methods. The methods described herein are less sensitive to the limitations of the optical analytical methods employed, since limitations of one detection method can be identified by and compensated for by the other optical detection method(s) employed. Using the detection methods described herein in parallel, the time required to definitively identify a target in a sample can be significantly reduced. Furthermore, careful selection of one or more of detection methods, illumination wavelengths, polarization of illuminating radiation, wavelength-specific optics, and instrument layout can reduce or eliminate interference between the detection methods employed. Selection of appropriate parameters depends on the sample and target (s) being assessed, and is within the ken of the skilled artisan in this field.

Raman Spectroscopy

Raman spectroscopy provides information about the vibrational state of molecules. Many molecules have atomic bonds capable of existing in a number of vibrational states. Such molecules are able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in wavelength can be more easily distinguished from the Rayleigh scattered light.

Because Raman spectroscopy is based on irradiation of a sample and detection of scattered radiation, it can be employed non-invasively and non-destructively, such that it is suitable for analysis of biological samples in situ. Little or no sample preparation is required. In addition, water exhibits very little Raman scattering, and Raman spectroscopy techniques can be readily performed in aqueous environments. Illumination of a sample over time can result in photobleaching of molecules in the sample, which can result in time-dependent fluctuations in fluorescence intensity following cessation of illumination. Low power, wide-field illumination of a sample over a period of more than a few seconds can substantially completely bleach the entire sample, allowing Raman and other measurements to be made against a non-fluctuating background, in contrast with scanning Raman spectroscopic measurements described in the art.

The Raman spectrum of a material can reveal the molecular composition of the material, including the specific functional groups present in organic and inorganic molecules. Raman spectroscopy is useful for detection of hazardous agents because most, if not all, of these agents exhibit characteristic 'fingerprint' Raman spectra, subject to various selection rules, by which the agent can be identified. A variety of Raman scattering properties, such as Raman peak position, peak shape, and adherence to selection rules, can be used to determine molecular identity and to determine conformational information (e.g., identity, viability, crystalline phase, degree of order, strain, grain size) for solid materials.

In the past several years, a number of key technologies have been introduced into wide use that have enabled scientists to largely overcome the problems inherent to Raman spectroscopy. These technologies include high efficiency solid-state lasers, efficient laser rejection filters, and silicon CCD detectors. In general, the wavelength and bandwidth of light used to illuminate the sample is not critical, so long as the other optical elements of the system operate in the same spectral range as the light source.

Because Raman scattering peaks are independent of the wavelength of the illumination source, the wavelength of light used to irradiate the cells is not critical. Illumination wavelengths less than 700 nanometers (e.g., from 350 to 695 nanometers), and likely as low as about 220 nanometers, can be used for Raman scattering analysis. An illumination wavelength of 532 nanometers is suitable, for example.

Because the intensity of scattered light is known to be dependent on the fourth power of the frequency (i.e., inverse wavelength) of the irradiating light, and only proportional to the intensity of the irradiating light, lowering the wavelength of the irradiating light can have the effect of increasing scattering signal output even if the intensity of the irradiating light is decreased. Thus, even under constant illumination, cells can survive irradiation if the intensity of the irradiating light is carefully controlled. Irradiation using shorter wavelengths (e.g., <about 500 nanometers, such as a wavelength of 220-280 nanometers) can be performed without harming the illuminated cells if intermittent or very short duration irradiation methods are employed. If survival of a target (e.g., a cell, a virus, or a toxin particle) in a sample beyond the time of detection is not important and so long as the Raman signature is preserved, then the effect of irradiating light on the hazardous agent need not be considered. However, it will be preferable in many instances to preserve the integrity of a target in a sample by illuminating the sample with radiation at a wavelength and intensity below the damage threshold for the target. In addition, background fluorescence in biological samples can generally be reduced by increasing the wavelength of the illuminating radiation.

In order to detect Raman scattered light and to accurately determine the Raman shift of that light, the sample should be irradiated with substantially monochromatic light, such as light having a bandwidth not greater than about 1.3 nanometers, and preferably not greater than 1.0, 0.50, or 0.25 nanometer. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light) can limit the ability to resolve, detect, or distinguish spectral features. The skilled artisan understands that and how the separation and shape of Raman scattering signals can determine the acceptable limits of spectral resolution for the system for any of the Raman spectral features described herein.

A field of illumination can be divided into multiple adjacent, non-adjacent, or overlapping points, and Raman scattering analysis can be assessed at each of the points. The points can be scanned serially (i.e., by scanning) or assessed in parallel (e.g., by assessing Raman scattering at each point at an RS value selected using a liquid crystal tunable filter and subsequently at a second RS value selected using the filter). To implement a scanning strategy, there is an inherent trade off between acquisition time and the spatial resolution of the spectroscopic map or image that is generated. Each full spectrum takes a certain time to collect. The more spectra collected per unit area of a sample, the higher the apparent resolution of the spectroscopic map, but the longer the data acquisition takes. Performing single point measurements on a grid over a field of view will also introduce sampling errors which makes a high definition image difficult or impossible to construct. Instead of scanning a sample, Raman scattering can be assessed in parallel (i.e., simultaneously) for all points in an image field. This parallel processing of all points is designated Raman chemical imaging, and can require significant computing time and capacity.

The computing and analysis resources required for Raman chemical imaging can be costly and bulky. An apparatus for Raman chemical imaging has been described by Treado in U.S. Pat. No. 6,002,476, and in U.S. patent application Ser. No. 09/619,371, filed 19 Jul. 2000, which are incorporated herein by reference. Other descriptions of Raman chemical imaging are U.S. patent application Ser. No. 09/800,953, filed 7 Mar. 2001; U.S. patent application Ser. No. 09/976,391, filed 21 Oct. 2001; U.S. patent application Ser. No. 10/185,090, filed 27 Jun. 2002; U.S. patent application Ser. No. 10/184,580 filed 27 Jun. 2002; U.S. provisional patent application 60/144,518, filed 19 Jul. 1999; U.S. provisional patent application 60/347,806, filed 10 Jan. 2002; U.S. provisional patent application 60/144,518, filed 19 Jul. 1999; U.S. provisional patent application 60/187,560, filed 28 Mar. 2000; U.S. provisional patent application 60/239,969, filed 13 Nov. 2000; U.S. provisional patent application 60/301,708 filed, 28 Jun. 2001; and U.S. provisional patent application 60/422,604, filed 21 Nov. 2002. Any of a variety of known methods can be used to correlate the Raman spectrum obtained at any particular point or averaged area with reference spectra. By way of example, standard spectral library comparison methods can be used to identify a component that occurs at a particular location in a sample. Alternatively, the spectral unmixing methods described in U.S. patent application Ser. No. 10/812,233, filed 29 Mar. 2004, can be used to identify multiple components present in an area of a sample. Each of the foregoing patents and applications is incorporated herein by reference.

In the methods described herein, portions of a sample in a field of view can be selected for Raman scattering analysis by first assessing the portions of the field that exhibit one or more optical properties characteristic of the hazardous agent. Sampling multiple points in an image allows variations in the Raman spectra to be observed and distinctions to be made as to components present in the various portions of the sample corresponding to the points. In this way, the processing time and resources needed to assess occurrence of the hazardous agent in the sample can be reduced or minimized. By way of example, regions of the image shown in FIG. 5B were assessed by Raman scattering analysis to identify the corresponding entities using the Raman spectra depicted in FIG. 5A.

Although Raman spectroscopy can generally be applied to samples on a wide variety of surfaces, some substrate materials are preferred relative to others. Ideal substrates are optically flat, Raman inactive (i.e., exhibit little or no Raman scattering), non-fluorescent, and can sustain large laser powers without exhibiting thermal expansion. Glass-based substrates are inexpensive, commonly used, and readily available. However, some glasses exhibit significant fluorescence emission(s) that are superimposed on the Raman spectrum. Although the Raman signal can be subtracted out of the sample spectra, such subtraction contributes to noise in the resulting signal. Further, in the presence of samples with a low Raman scattering cross section (e.g., a small number of BG spores) a high background signal (e.g., that attributable to glass fluorescence) can overwhelm the Raman signal attributable to the sample. In such instances, it can be difficult to subtract out the background to reveal the sample signal. Fused silica (i.e., optical grade quartz) is an alternative often used by Raman spectroscopists, because it does not exhibit the significant fluorescence background of glass. Fused silica is also colorless and clear, allowing traditional transmittance optical viewing. Fused silica exhibits a limited Raman signal that must be subtracted from the final spectrum. Although this may present some signal-to-noise ratio problems (e.g., at very low Raman scattering cross sections), the lower background signal reduces the chance of the background signal overwhelming the sample signal, relative to glass-based substrates.

A preferred substrate is an aluminum oxide-based filter (e.g., ANODISC® brand aluminum oxide filtration membranes available from Whatman PLC, Brentford, Middlesex, UK). The ANODISC® filter exhibits a relatively weak Raman signature, is non-fluorescent, and can sustain large laser power densities without undergoing thermal expansion. Some residual spectroscopic properties of the substrate requires corrective steps to subtract its signature from the overall sample spectroscopic response, but this can be achieved using known methods. Another preferred substrate, particularly for ambient air sampling, is the micro-orifice uniform deposit impactor (MOUDI™ available from MSP Corporation, Shoreview, Minn.). This device exhibits favorable background properties. The MOUDI™ sampler collects ambient particulate material and deposits the material onto a flat, smooth aluminum foil substrate satisfactory for both Raman and scanning electron microscopic and energy dispersive spectrometric measurements.

Other Optical and Spectroscopic Methods

One or more of a variety of methods can be used to identify areas of a sample or entities in a sample for which Raman scattering analysis should be performed (or, conversely, need not be performed). Preferably, the optical or spectroscopic method(s) used for this purpose can be performed significantly more rapidly than Raman scattering analysis. Examples of suitable methods include absorbance, fluorescence, diffraction, polarization, and microscopic methods. In one embodiment, the sample (or at least a field of view of the sample) is illuminated with radiation that can be used in more than one optical and/or spectroscopic method (e.g., incident laser light useful for Raman scattering, fluorescence spectroscopy, and optical microscopy). Examples of suitable microscopic methods include scanning electron microscopy, differential interference contrast microscopy, brightfield reflectance microscopy, polarized light microscopy, and fluorescence microscopy. Microscopic methods can be used for assessing the morphology of entities in a sample, In fluorescence spectroscopy, photons are emitted from a material following an excitation step in which absorption of photons occurs. Experiments typically include a polychromatic excitation source such as mercury (Hg) or xenon (Xe) lamps or a monochromatic source such as a light-emitting diode (LED) or laser for sample excitation. A portion of the emitted radiation may then be directed into a dispersive monochromator to which a detector device such as a CCD is attached. By measuring the fluorescence spectrum from a material, one can deduce qualitative and quantitative information from inorganic and organic species. In comparison to Raman spectroscopy, fluorescence is inherently more sensitive. Detection limits in the parts-per-billion range are common. On the other hand, fluorescence is less selective than Raman and there are a limited number of chemical systems that exhibit fluorescence. Nonetheless, fluorescence analysis can be performed much more rapidly than Raman scattering analysis.

Fluorescence analysis can distinguish biotic and non-biotic materials, which can be advantageous for identifying entities in a sample that are not living. If detection of a living hazardous agent (e.g., a pathogenic bacterium or eukaryote) or a viral agent is desired, fluorescence analysis is a suitable method for excluding sample entities from slower Raman scattering analysis. Suitable parameters for fluorescent analysis of biotic materials are known. By way of example, such parameters are described in Pinnick et al. (1999, Field Anal. Chem. Technol. 3:221-239).

Molecular UV/visible and NIR absorption spectroscopies involve the absorption of photons in the UV/visible (185-780 nanometer (54,054 to 12,800 cm$^{-1}$)) and NIR (780 nanometer to 2.5 micrometer (12,800 to 4,000 cm$^{-1}$)) spectral regions, respectively. Typical instrumentation include a polychromatic source such as a deuterium or quartz tungsten halogen lamp, a dispersive element such as a monochromator or interferometer, and a detection device such as a Si CCD or InGaAs focal plane array detector. As with other optical methods described herein, the wavelength and intensity of illuminating radiation should be selected to avoid unacceptable sample or target degradation. Longer wavelengths, such as NIR radiation, can enhance penetration into a sample, permitting analysis of non-surface materials.

Absorption measurements based upon UV-visible or NIR radiation have many known applications for qualitative and quantitative determination of inorganic and organic chemical species. NIR spectra result from the overtone and combination bands of fundamental mid-infrared (MIR) bands. Like fluorescence, absorption spectroscopies are highly sensitive but only moderately selective. Absorption phenomena can also yield information about the chemical identities of the materials present in a sample. To the extent specific absorbance information about a target of interest is known, analysis of radiation absorbed by a sample can be informative regarding the occurrence of that target in the sample. Absorption spectroscopy is a useful method for identifying entities in a sample for which Raman scattering analysis need not be performed. Conversely, absorption spectroscopy can be used to identify areas of a sample or entities within a sample for which Raman analysis should be performed.

Spectroscopic methods can be extended to imaging techniques through the use of imaging spectrometers such as liquid crystal imaging spectrometers. The development of this technology in recent years has enabled spectroscopic imaging to develop and mature.

Spectroscopic imaging is a versatile technique that is well suited to the analysis of complex heterogeneous materials. Applications of spectroscopic imaging range from the analysis of polymer blends, defect status analysis in semiconductor materials, inclusions in human breast tissue, characterization of corrosion samples and detection, and classification and identification of BWAs and CWAs. Spectroscopic imaging provides a potential solution for obtaining both qualitative and quantitative image information about molecular composition and morphology of BWAs and CWAs, allowing a more accurate and more rapid analysis than traditional imaging or 'wet' chemical methods.

Optical and fluorescent microscopy techniques are well suited for identifying entities in a sample that are, or are not, characteristic of certain hazardous agents. For example, many bacteria, bacterial spores, eukaryotic cells, and viruses have a characteristic size, shape, or arrangement (e.g., chains, sheets, or groups). Microscopic methods can be performed rapidly and the results obtained thereby can be rapidly assessed using known methodologies to assess the size, shape, arrangement, or other morphological characteristics of entities in a field of view. Microscopic methods are therefore suitable for assessing optical properties of entities in a sample in order to exclude from Raman scattering analysis entities that do not have morphological properties, fluorescent properties, or both, that are characteristic of the hazardous agent. The same methods can be used to identify entities for which Raman scattering analysis should be performed.

Figure 4A:
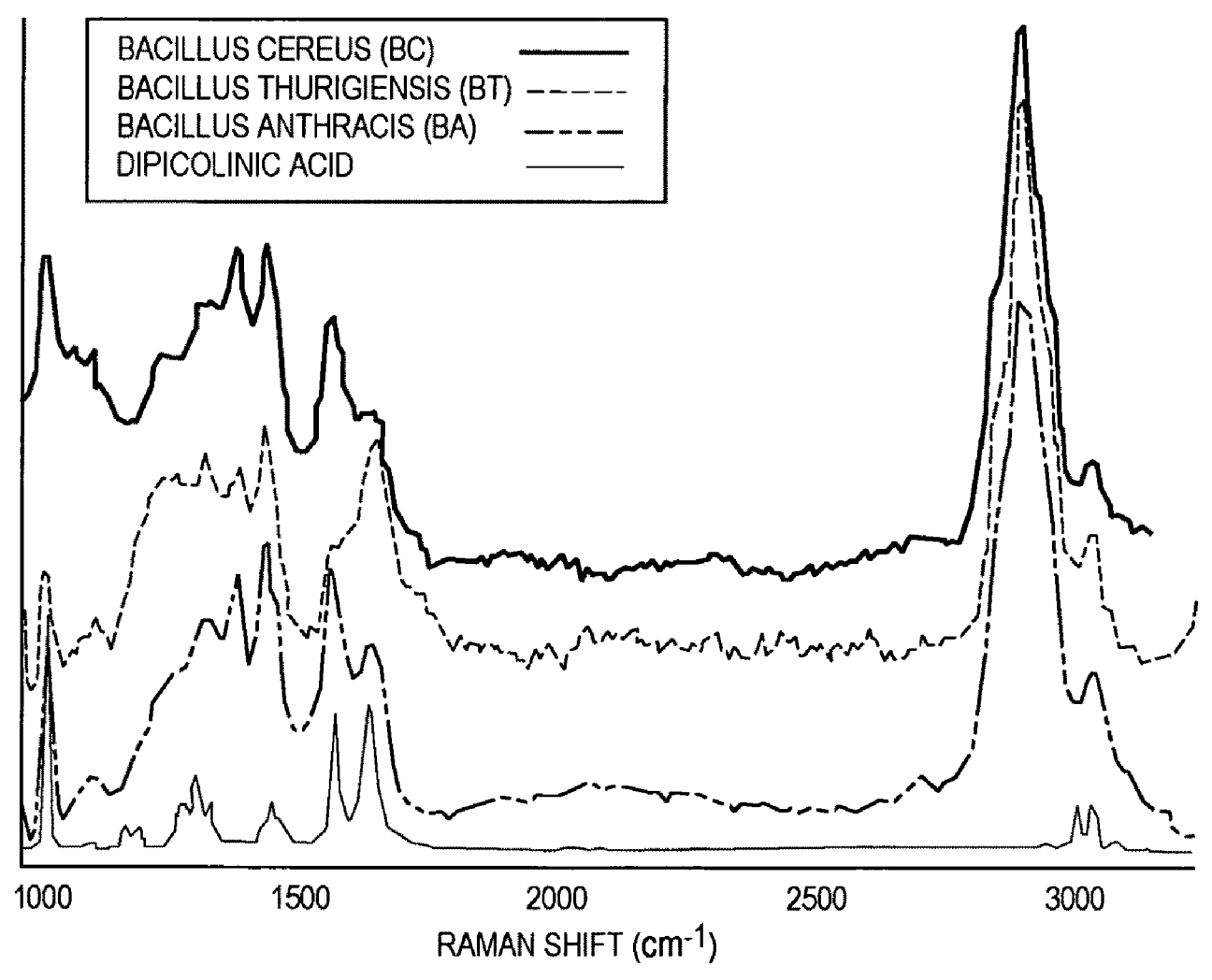
Figure 4B:
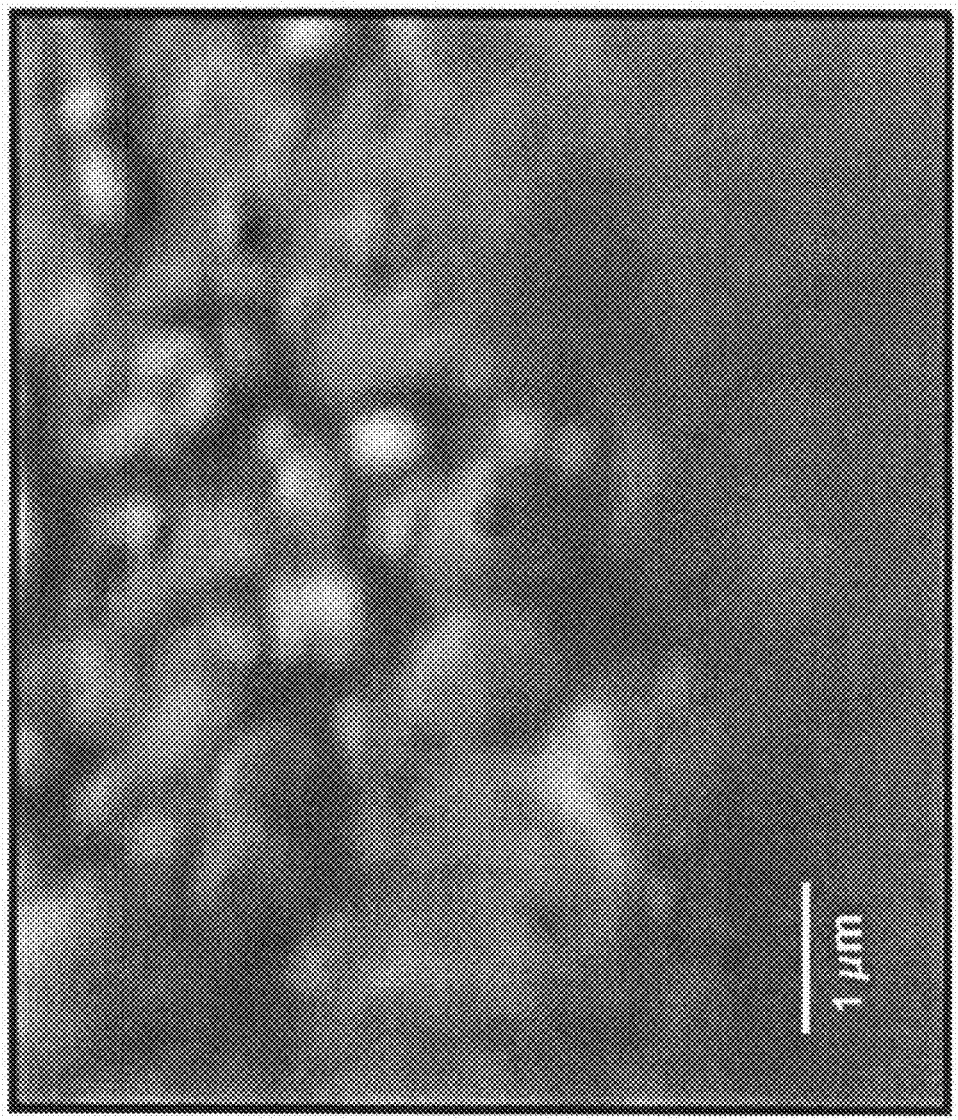
FIG. 4B is a microscopic image of *Bacillus anthracis*.

FIG. 4B shows a typical magnified view of a sample containing *Bacillus anthracis*. The spectra shown include a Raman spectrum corresponding to *B. anthracis*. The differences which are evident between the spectrum of *B. anthracis* and the spectra of the other *Bacillus* species demonstrate that *B. anthracis* can be differentiated from those species in a sample containing all three samples. This can performed by i) analyzing the sample in a microscopic field of view by visible light reflectance microscopy to identify entities that have the size, shape, or both, characteristic of a *Bacillus* (i.e., oblong shape with characteristic dimensions); ii) analyzing those entities to see which fluoresce (e.g., using excitation radiation having a wavelength of 365 nanometers and assessing visible fluorescence) and are therefore likely biotic; and iii) analyzing the Raman spectrum of individual fluorescent *Bacillus*-sized and/or -shaped entities to assign an identity to the entity, based on similarity to known Raman spectra such as those shown in FIG. 4A. The Raman spectroscopy step can be performed by assessing light scattered at a single pixel corresponding to the entity, by assessing light scattered from a group of pixels corresponding to the entity, or by assessing light scattered from one or more areas that include some or all of the entity.

Discriminating Suspect Entities from Other Entities

A significant advantage of the methods described herein relative to previously described Raman spectral analytical methods is that the time required for Raman analysis can be significantly shortened by excluding from Raman analysis entities in a sample that do not exhibit one or more optical properties of a hazardous agent. Sampling multiple points in an image allows variations in the Raman spectra to be observed and distinctions to be made as to components present in the various portions of the sample corresponding to the points. Acquiring Raman scattering data at every position and analyzing the spectra at every point in an image would require significantly greater time. Instrument power and computing resources can thereby be concentrated on areas of a sample most likely to contain the hazardous agent.

The methods described herein are amenable to automation, in that the analysis of optical properties and Raman spectra can be performed using computer software as well as manually. Characterization of an optical field based on single optical properties corresponding to specific locations within the field (i.e., image analysis for absorbance at a selected wavelength) is routine in the art. For example, in one embodiment, if the presence or absence of bacterial spores are to be analyzed, then assessment of fluorescence should be performed by analyzing discrete areas of the optical field having a size not greater than 2, 3, 5, 10, or 25 times the cross-sectional area of a single spore. Further by way of examples, bacteria and their spores have characteristic dimensions that are typically on the order of one to several micrometers, viruses have characteristic dimensions that are on the order of tens to hundreds of nanometers, and eukaryotic cells have characteristic dimensions that are on the order of ten micrometers. Any of a variety of known digital image processing techniques can be used to characterize the size, shape, and spatial distribution of entities in a visible or fluorescent microscopic field. The characteristic dimensions of chemical agents, including biological toxins, depend on their agglomeration, crystallization, or other associative characteristics. The characteristic size of analytes can also depend on sample components other than the analyte itself.

Wide field Raman scattering analysis is also amenable as a method of identifying regions of an optical field that warrant higher definition Raman scattering analysis. When the area of a sample corresponding to a point at which a Raman spectrum is assessed is much larger than a characteristic dimension of an analyte or an analyte-containing particle, the methods described herein can still be employed. In that instance, the results obtained using the method will be indicative of the presence of the analyte in a region of the sample, rather than pinpointing the location of a discrete particle of the analyte. Such regions of the sample can be subjected to further analysis once identified. A skilled artisan will understand how to select appropriate point sizes based on the desired analyte.

Multimodal spectral sensing can employ substantially any optical or spectroscopic method for identifying regions of a sample or entities within a sample that do not warrant more detailed and time-consuming Raman spectral analysis. Examples of such methods include fluorescence, UV/visible absorption/reflectance, NIR absorption/reflectance, and wide-field Raman spectroscopies. Contrast can be generated in the images by superimposing, adding, or otherwise combining spectral information obtained by these spectroscopic methods. The display and/or correlation of these different information sets is referred to herein as image fusion. Because a spectrum is generated for each location assessed, chemometric analysis tools such as correlation analysis, principal component analysis (PCA), and factor rotation, including multivariate curve resolution (MCR), can be applied to the image data to extract pertinent information that might be less obvious by analyzing ordinary univariate measures.

Depending on the materials and the spectroscopic method(s) used, depth-related information can also be obtained by using different excitation wavelengths or by capturing spectroscopic images at incremental planes of focus. Thus, depending on the penetrating ability of illumination and detected wavelengths, the contents of objects (e.g., vials, envelopes, or suitcases) can be assessed using these methods.

A spatial resolving power of approximately 250 nanometers has been demonstrated for Raman spectroscopic imaging using visible laser wavelengths with commercially available equipment. This is almost two orders of magnitude better than infrared imaging, which is typically limited to resolution not less than 20 micrometers, owing to diffraction for example.

An advantage of using NIR radiation in multimodal spectral sensing is that it penetrates more deeply than visible light so as to enable one to probe inside of paper or plastic envelopes or plastic or glass containers, for example to detect a hazardous agent in the container. Any container that does not totally absorb the incident radiation can be examined using the NIR multimodal spectral sensing approach.

Another way of discriminating potential hazardous agents from other entities in a sample is by assessing Raman scattered radiation at a single Raman shifted wavelength characteristic of the hazardous agent. Areas of the sample from which radiation having a Raman shift (relative to incident radiation) characteristic of the hazardous agent is scattered can be selected for more detailed Raman spectral analysis. Thus, in one embodiment, a sample is assessed by identifying one or more portions of a microscopic field from which Raman scattered radiation characteristic of a hazardous agent of interest emanates, and thereafter assessing a Raman scattering spectrum of those portions. Of course, the portions can also be scanned using other optical methods (e.g., optical microscopy or fluorescence spectroscopy, as described above) to reduce the number of portions for which Raman spectra are collected and to thereby enhance the speed of the process.

Image Fusion

Spectroscopic information obtained by two or more spectroscopic methods as described herein can be combined and stored, displayed, or both, as a single data set. By way of example, Raman-scattered light detected from a sample can be amplified (or falsely colored) and displayed together with a visible microscopic image of the sample. In addition, fluorescent light emitted by the sample can be displayed in the same image.

Fusion of spectroscopic information obtained from a single field of view by two or more spectroscopic methods requires mapping of the information obtained by each method to identical or overlapping elements of a data set. By way of example, a visual image can be made by displaying numerous picture elements having a known relationship to one another. For each spectroscopic method for which information is to be represented in the image, the spectroscopic information obtained from a portion of a sample must be mapped to the picture element(s) corresponding to that portion. Information from different spectroscopic methods can be displayed in a picture element corresponding to the same portion of the sample by representing each spectroscopic measurement by an independent variable of light displayed at the picture element. By way of example, a color image based on the Hunter color scale can be generated by (for each picture element of the image): i} representing brightness assessed by visible light microscopy as luminosity (L) on the Hunter color scale; ii} representing fluorescent intensity at a selected wavelength assessed by fluorescence spectroscopy as red-ness (a) on the Hunter color scale; and iii} representing the intensity of Raman-scattered light at a selected RS value as yellow ness (b) on the Hunter color scale. This display methodology is merely an example. Substantially any method of representing independent data sets in a single image or data structure can be used. What is important is that the spectroscopic information obtained from a discrete portion of the sample by multiple spectroscopic methods be mappable to the portion of the sample from which it was obtained, and that the method of storing or displaying that information preserve the mapping, so that different spectroscopic properties of the portion can be correlated.

EXAMPLES

The invention is now described with reference to the following Examples. These Examples are provided for the purpose of illustration only, and the invention is not limited to these Examples, but rather encompasses all variations which are evident as a result of the teaching provided herein.

Rapid Hazardous Agent Detection System

A hazardous agent detection system having the configuration shown in FIG. 1 can be constructed using ordinary skill in view of this disclosure. Such systems can be used or modified as described herein to meet the instrument requirements of the methods described herein for multimodal spectral analysis. Such configurations can include platforms based on a microscope, a macroscope, an endoscope, a fiber array spectral translator (FAST), or an environmental (e.g., air or water) sampler designs. Each of these is outlined in the following sections.

In FIG. 1, excitation sources 110, 120, 130, and 140 (corresponding to near infrared, infrared, visible, and ultraviolet sources, any combination of which can be present) provide incident radiation that is directed by input transfer optics 200 onto a sample that is situated in an sample cell 210. The sample cell 210 can optionally be integrated with one or more other elements of the device, such as the input transfer optics 200. Such integrated sample cells can be employed as single-use (i.e., disposable) sample containers, which can be discarded, incinerated, or archived. The excitation sources can be substantially any known radiation source, including polychromatic sources such as tungsten or mercury arc lamps and substantially monochromatic sources such as lasers.

Radiation transmitted through, or reflected, refracted, emitted, or scattered by the sample is collected using output transfer optics 220 selected and situated to be appropriate for the radiation to be collected. The collected radiation is directed to appropriate detectors, and the output of the detectors (informative of the collected radiation) is captured by a data recordation circuit or device, which can be physically and/or electronically integrated with the detectors (as in the integrated optical detectors and data capture subsystem 300 depicted in FIG. 1).

Data collected from the detectors is preferably fed into a data analysis subsystem 400 within or linked to a computer 450. The computer can be operated with software for controlling illumination, data collection, sample positioning, and the like, and such software is within the ordinary level of skill in this field and commercially available. The computer preferably links input 410, display 420 (e.g., a visual display such as a video display terminal or printable image), and data storage 430 functions with the optical device(s), and also preferably is able to format output/results 500 in a way convenient for the user. By way of example, in a system for hazardous agent detection on a sample collection substrate fed continuously into the sample cell 210, the computer 450 may conveniently provide output 500 that indicates the number of entities that are detected on the substrate as having Raman spectral characteristics of the hazardous agent of interest during a given period of time. Further, the output 500 may trigger an alarm circuit if the number of hazardous agent entities (e.g., pathogenic microorganisms or regions in which a chemical agent occurs) detected during a period of time (or during multiple consecutive periods of time) exceeds a pre-selected value. Alternatively, data collected from the detectors can be displayed for analysis by a user, and portions of the sample can be selected by the user for Raman scattering analysis. A controller (e.g., computer 450) coupled to a Raman detector may be used for restricting detection of Raman-shifted radiation to entities for which an optical property characteristic of the pathogen was previously detected.

An example of a commercially available device which is suitable for use in one or more of the platforms is a laboratory or transportable field Raman microscope such as the FALCON Raman microscope (TM; ChemImage Corporation, Pittsburgh, Pa.), or a ChemImage Corporation EAGLE™ field-hardened instrument, outfitted with the simultaneous imaging and spectroscopy apparatus offered by that supplier for use with the instrument. Another example of a suitable instrument upon which such systems can be based is an ultraviolet (UV)/visible (vis)/near infrared (NIR) fluorescence or Raman macroscope, or a UV/Vis/NIR/Mid-IR (mid-infrared) absorption/reflectance macroscope system such as the CONDOR Macroscope (TM; ChemImage Corporation, Pittsburgh, Pa.). Another suitable device is a laboratory or field fiberscope such as the RAVEN endoscope (TM; ChemImage Corporation, Pittsburgh, Pa.). Other suitable devices are described in U.S. Pat. No. 6,002,476. Any of these instruments can be used alone or with additional optics, such as a laboratory or field Fiber-Array Spectral Translator (FAST) probe. Each of the modes of application can be used separately or in combination with one another to achieve the desired speed and results.

By way of example, an air sampling biothreat detector can be constructed by combining several components. A sampler or collector element can be used to gather particulates and/or aerosols from an air sample. The collected particles can be deposited on a surface suitable as a substrate for Raman and other optical analysis. The surface can be a continuous sheet of material which is advanced constantly, intermittently, or at will in front of the optical detection systems described herein. Optionally, the particles can be sorted (e.g., electrostatically) prior to deposition on the substrate. The results obtained using the optical detection systems (e.g., optical microscopy to determine particle morphology, fluorescence imaging to determine biological or non-biological origin, and Raman spectroscopy or imaging to identify particular entities identified as suspicious by optical and/or fluorescent analysis), can be recorded, transmitted, or used to perform logic operations (e.g., activating an alarm upon the detection of a target of interest).

These systems can be automated through the use of robotics or combined macro/micro instrumentation in order to target analytes of interest. Using laser ablation and/or chemical ablation, the system can be automated to eradicate hazardous agents post-targeting, for example. Such a system should provide fast acquisition times (on the order of seconds), high spatial resolution (sub-micron), and good spectral resolution (<200 nanometers).

Microscope-Based System

The multimodal spectroscopic imaging microscope combines in a single platform a solid state laser for sample excitation (e.g., for Raman and laser-induced fluorescence), a refractive optical microscope base, which is equipped with infinity-corrected microscope objectives, an automated XYZ translational microscope stage, and a quartz tungsten halogen (QTH) lamp and/or a mercury (Hg) lamp. Also a part of the microscope system is an analog color charge-coupled device (CCD) detector for ordinary optical image collection and digital image collection, a liquid crystal spectrometer or other multi-point spectrometer technology including AOTF, scanned linearly variable or rotated circularly variable dielectric filters, angle-rotated Fabry Perot dielectric or other bandpass filter, interferometers including Michelson and Zagnac types, or dispersive spectrometers. Also included is either a room temperature or optionally cooled photomultiplier, IR FPA for IR image capture, or a thermoelectrically cooled (TE) silicon (Si) CCD (i.e., TE Si CCD) or complementary metal oxide semiconductor (CMOS) detector for UV/visible, Raman and fluorescence data capture, and a remote, dispersive monochromator equipped with a CCD or CMOS detector for single point or multi-point dispersive spectral collection.

UV, visible, or NIR illumination is directed to the sample in a reflected light configuration using a QTH source or other broadband white light source, including metal halide, Hg arc lamps, or Xe arc lamps or a transmitted light configuration using QTH or other suitable source of a refractive optical microscope platform. In a Raman or laser-induced fluorescence experiment, laser radiation is introduced to the sample through use of a Raman illuminator. Light scattered, emitted, reflected, or transmitted is collected from the sample positioned on the automated XYZ translational microscope stage through an infinity-corrected microscope objective.

Ordinary optical imagery of the sample can be obtained using a mirror or using a beamsplitter or prism arrangement inserted into a turret wheel of the microscope by collecting an image with an analog or digital color or monochrome CCD or CMOS detector. In spectroscopic imaging mode, the magnified spectroscopic image is coupled through an imaging spectrometer and collected on a NIR or mid-IR focal plane array (FPA) detector (for IR spectroscopic imaging) or a Si CCD detector (for UV/visible absorption/reflectance, fluorescence, or Raman spectroscopic imaging). The IR FPA is typically comprised of indium gallium arsenide (InGaAs), but may be comprised of other IR sensitive materials, including platinum silicide (PtSi), indium antimonide (InSb), or mercury cadmium telluride (HgCdTe). Suitable FPA detectors are known in the art.

A central processing unit, such a PENTIUM® processor-based computer, can be used for control of spectroscopic image collection and processing. The analog color CCD, IR FPA, Si CCD, automated XYZ translational microscope stage, a liquid crystal tunable filter, an imaging spectrometer, other components of the instruments, or some combination of these can be controlled by the computer. Commercial software packages, such as CHEMACQUIRE (TM; ChemImage Corporation, Pittsburgh, Pa.), CHEMANALYZE (TM; ChemImage Corporation, Pittsburgh, Pa.), and CHEMIMAGE XPERT (TM; ChemImage Corporation, Pittsburgh, Pa.) are available for such control, and it is within the ordinary level of skill in this field to modify existing software or generate new software for control of the instruments described herein.

By including a polarization sensitive beam splitting element in the optical path prior to the liquid crystal imaging spectrometer, a portion of the signal from the sample may be coupled to a remote dispersive spectrometer. This allows conventional spectroscopic tools to be used to gather spectra for traditional, high-speed spectral analysis. The spectrometers can include one or more of the following types: fixed filter spectrometers; grating based spectrometers; Fourier transform spectrometers; and acousto-optic spectrometers. A polarization independent interferometer such as a Michelson interferometer, a Sagnac interferometer, a Twynam-Green Interferometer, or a Mach-Zehnder Interferometer can be used as a filter.

Liquid crystal (LC) sensing spectrometer technology is used for wavelength selection. The LC sensing spectrometer may be of the following types: Lyot liquid crystal tunable filter (LCTF); Evans Split-Element LCTF; Solc LCTF; Ferroelectric LCTF; Liquid crystal Fabry Perot (LCFP); or a hybrid filter technology comprised of a combination of the above-mentioned LC filter types. Additionally, fixed bandpass and band rejection filters comprised of dielectric, rugate, holographic, color absorption, acousto-optic, or polarization types may also be used, either alone or in combination with one of the above LC spectrometers. Novel tunable filter designs identified as bi-refringent interference spectrally agile filter element (BISAFE) as well as micro-opto-electro-mechanical (MOEM) based spectrometers have characteristics that enable multi-point imaging with a smaller form factor than conventional filter designs and are suitable for use in handheld and portable devices.

New solid state multi-point detector designs can reduce the cost of the detector without compromising the ability to perform multi-point spectral sensing. The BISAFE filter, which is described in co-pending U.S. patent application Ser. No. 10/893,331, filed on 19 Jul. 2004 and in U.S. provisional patent application No. 60/488,246, filed on 18 Jul. 2003, is a linearly tunable filter that allows line imaging. Spectral data is obtained in different spectral ranges and at different locations (i.e., lines) of the sample simultaneously. Similarly, the MOEMS filter, which is described in co-pending U.S. patent application Ser. No. 10/893,332, filed on 19 Jul. 2004 and in U.S. provisional patent application No. 60/488,246, filed on 18 Jul. 2003, senses different spectral regions along strips of the silicon plates forming this MOEMS device. These strips define the regions selected on the sample by positioning plates using MEMS microactuators. Images can be reconstructed (if desired) by stepping the sample position. This device can operate either in a transmission mode, in which the light travels parallel to the substrate and normal to the Si plates, or in a transmission-reflection mode, in which light travels normal to the substrate and normal to the silicon plates. Such devices allow a trade-off between selection of spatial position or spectral resolution in a simple design.

Grating spectrometers can be used with FAST technology for wavelength and multi-point spectra collection. Such spectrometers allow a plurality (e.g., a group or line) of points along the sample to be sampled at each wavelength setting of the spectrometer during each measurement. This allows efficient data collection of many points at the same time, thereby providing many spatially distinct spectra to be obtained at once during one scan over the spectral regions of interest.

The multimodal spectral sensing microscope can also be used as a volumetric imaging instrument by moving the sample through the focus plane in the Z-axial dimension (i.e., in a direction normal to the 2-dimensional X/Y plane of image analysis), collecting images in and out of focus, and reconstructing a volumetric data of the sample using appropriate software, which is commercially available and/or within the ordinary level of skill in this field. For samples having significant volume (e.g., bulk materials, surfaces, interfaces, and phase contact regions), volumetric spectroscopic reconstruction is useful for failure analysis, product development, and routine quality monitoring. Quantitative analysis can be performed simultaneously with volumetric analysis. Volumetric analysis can be performed in a non-contact mode without modifying the sample by using numerical confocal techniques, which require that the sample be sensed at discrete focal planes. Computational optical sectioning reconstruction techniques based on a variety of strategies have been demonstrated, including nearest neighbors and iterative deconvolution, and such computational methods are suitable for use with the devices and methods described herein.

Microscope-based spectroscopic sensing systems have the advantage of being able to detect, classify, identify, and visualize entities such as BWAs at the level of a single bacterium, for instance. These systems exhibit a spectral resolution on the order of 8 $cm^{-1}$ and a spatial resolution of approximately 200 nanometers using numerical deconvolution methods.

Macroscope-Based System

The spectroscopic multimodal sensing macroscope combines in a single platform an illumination subassembly consisting of an illumination source (e.g., a QTH, Xe, Hg, or metal halide lamp), a barrier optical filter(s), and a light-directing module (e.g., direct beam, fiber optic, or liquid light guide illumination). A radiation detector such as an analog color CCD detector is used for optical and digital image collection. Wavelength selection can be performed using a liquid crystal tunable filter or multi-point spectrometer. The imaging detector can be a room temperature (or optionally cooled) NIR FPA (for NIR image capture) or a room temperature or thermoelectrically cooled Si CCD detector (for UV/visible and fluorescence image capture), for example.

UV, visible, or NIR illumination is directed to the sample in a reflected light configuration using a QTH source or other broadband white light source, including metal halide, Hg arc lamps, or Xe arc lamps or a in transmitted light configuration using QTH or other suitable source through direct illumination, fiber optics, or liquid light guides. Light emitted, reflected, or transmitted is collected from the sample positioned on the macroscopic sample base through a macro lens.

Ordinary optical imagery of the sample may be obtained using a mirror or beamsplitter or prism arrangement inserted into the collection stack of the macroscope and collecting an image with an analog or digital color or monochrome CCD or CMOS detector. In spectroscopic mode, the spectroscopic points sampled are coupled through a liquid crystal spectrometer and collected on a NIR FPA detector (for NIR spectroscopic imaging) or a Si CCD detector (for UV/visible absorption/reflectance, fluorescence, and Raman spectroscopic imaging). A computer, such as a PENTIUM® processor-based computer, can be used for multimodal spectroscopic data collection and processing as described herein.

Liquid crystal (LC) spectrometer technology can be used for wavelength selection. The LC spectrometer can be of any of the types described herein. Additionally, fixed bandpass and bandreject filters of the types described herein can be used, either alone or in combination with an LC spectrometer. These filters can select an arbitrary or random set of points for sampling or a well defined set of points determined by the sampling approach and/or the requirements for high performance of the spectrometer. For example, a resistive anode array used as a photon detector favors selection of linear points along the sample. Similarly, a FAST array can be arranged in linear fashion or another collection geometry to facilitate data acquisition.

Grating spectrometers can be used in the FAST configuration for wavelength and multi-point spectra collection. Such spectrometers used with FAST technology allow an arbitrary arrangement of points on the sample to be sampled at each wavelength setting of the spectrometer. This permits efficient data collection of many points at the same time and collection of spatially distinct spectra during a single scan over the spectral regions of interest.

Figure 3:
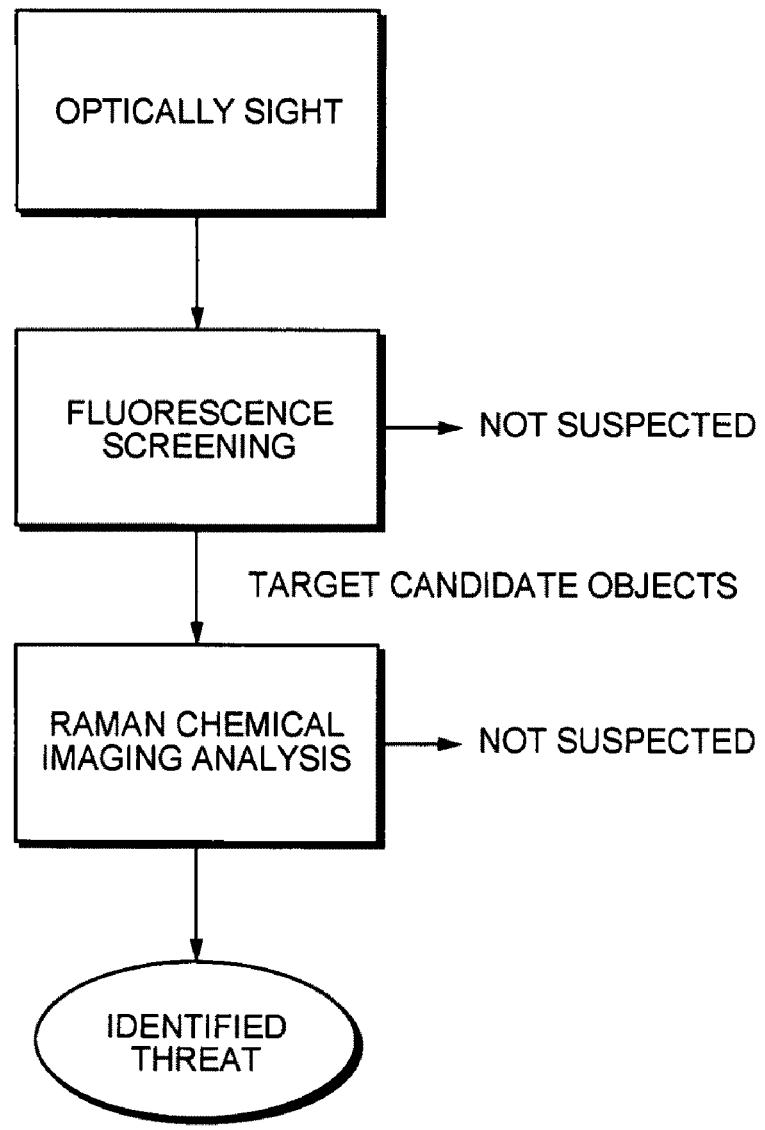
FIG. 3 is a flow chart which depicts one embodiment of the multimodal analytical methods described herein for identification of threat entities such as BWAs or CWAs.

A macroscope-based system enables rapid detection of potential hazardous agents over a large area, such as the surfaces and contents of envelopes and packages received by mail and analysis of surfaces in remote locations. In multi-modal detection, rapid sample analysis strategies (e.g., fluorescence imaging when analyzing the presence of hazardous agents) are preferably performed early in the analytical process to more rapidly isolate the points of highest interest for subsequent detailed analysis. An example of this methodology is depicted in FIG. 3. The macroscope can be used to optically sight sample areas which appear suspect. Fluorescence screening of the selected area can indicate portions which do not fluoresce, and therefore do not appear to be of biological origin. Fluorescing portions of the selected area (or entities within that area) can be further analyzed by Raman chemical imaging to differentiate potential biological threats from non-threatening entities.

Endoscope-Based System

Spectroscopic sensing has traditionally been performed in laboratory settings using research-grade light microscope technology as an image-gathering platform for selection of specific points. However, multimodal spectroscopic sensing is also applicable to in situ industrial process monitoring and in vivo clinical analysis. The application of multimodal spectroscopic sensing outside the research laboratory has been limited by the lack of availability of stable spectroscopic and/or optical selection/detection platforms that are compatible with the physical-demands of industrial process monitoring and clinical environments. Both industrial and clinical settings often require compact, lightweight instrumentation suitable for the examination of remote areas that are inaccessible to conventional spectroscopic instrumentation.

A robust spectroscopic multimodal design employing liquid crystal technology has been described herein, and the equipment, systems, and methods described herein can be employed using fiber optic technology suitable for fashioning into a flexible probe such as an endoscope. The liquid crystal endoscope is the first flexible multi-point endoscopic technology that provides real-time video inspection capability with spectral analysis. The endoscope, comprising from two to thousands of independent fibers arranged in a fiber bundle, couples to a video CCD for real-time video imaging of the analysis area. This allows for quick visual screening of the sample. The endoscope tip is engineered to filter laser illumination and collect Raman scattered radiation and fluorescent emissions (for Raman and fluorescence applications). The light from the laser delivery fiber is filtered so that substantially only the laser wavelength is presented to the sample. The laser light is removed from the collected light so that Raman information is detectable to within 200 cm$^{-1}$ of the laser line.

The distal end of the liquid crystal Raman endoscope is environmentally resistant and can withstand continuous operation at high temperatures and has been demonstrated to operate from 0 to 315 degrees Celsius while maintaining high signal to background performance. The distal end can be coupled to a microscope-based system enabling dispersive spectroscopy and multi-point spectroscopic sensing to be performed remotely.

An endoscope-based spectroscopic sensing system is useful for detecting the presence of a hazardous agent in a remote location, such as the interior of a box or envelope, for example.

FAST-Based System

An emerging technology in the field of spectroscopic imaging is the use of fiber optic arrays. We have termed this technology Fiber Array Spectral Translators (FAST) but it is also accurately described as dimension reduction arrays. FAST technology can acquire a few to thousands of full spectral range, spatially resolved spectra simultaneously. For imaging this is done by focusing a spectroscopic image onto a two dimensional array of optical fibers that are drawn into a one-dimensional distal array with serpentine ordering. The one dimensional fiber stack is coupled to an imaging spectrograph. Software then extracts the spectral/spatial information that is embedded in a single CCD image frame. Fiber array spectroscopic imaging has been demonstrated in several applications including Raman chemical imaging analysis of micro-composites and biomaterials and time-resolved atomic emission chemical imaging of laser-induced plumes.

An advantage of this method over other current point spectroscopic detection methods is speed of analysis. A complete spectroscopic data set can be acquired in the amount of time it takes to generate a single spectrum from a given material. Even with limited pixel definition, comparing low-resolution spectral data with high-spatial resolution optical images can provide significant insight into the morphology and chemistry of the materials in the field of view.

Ambient Air Sensor System

Figure 2:
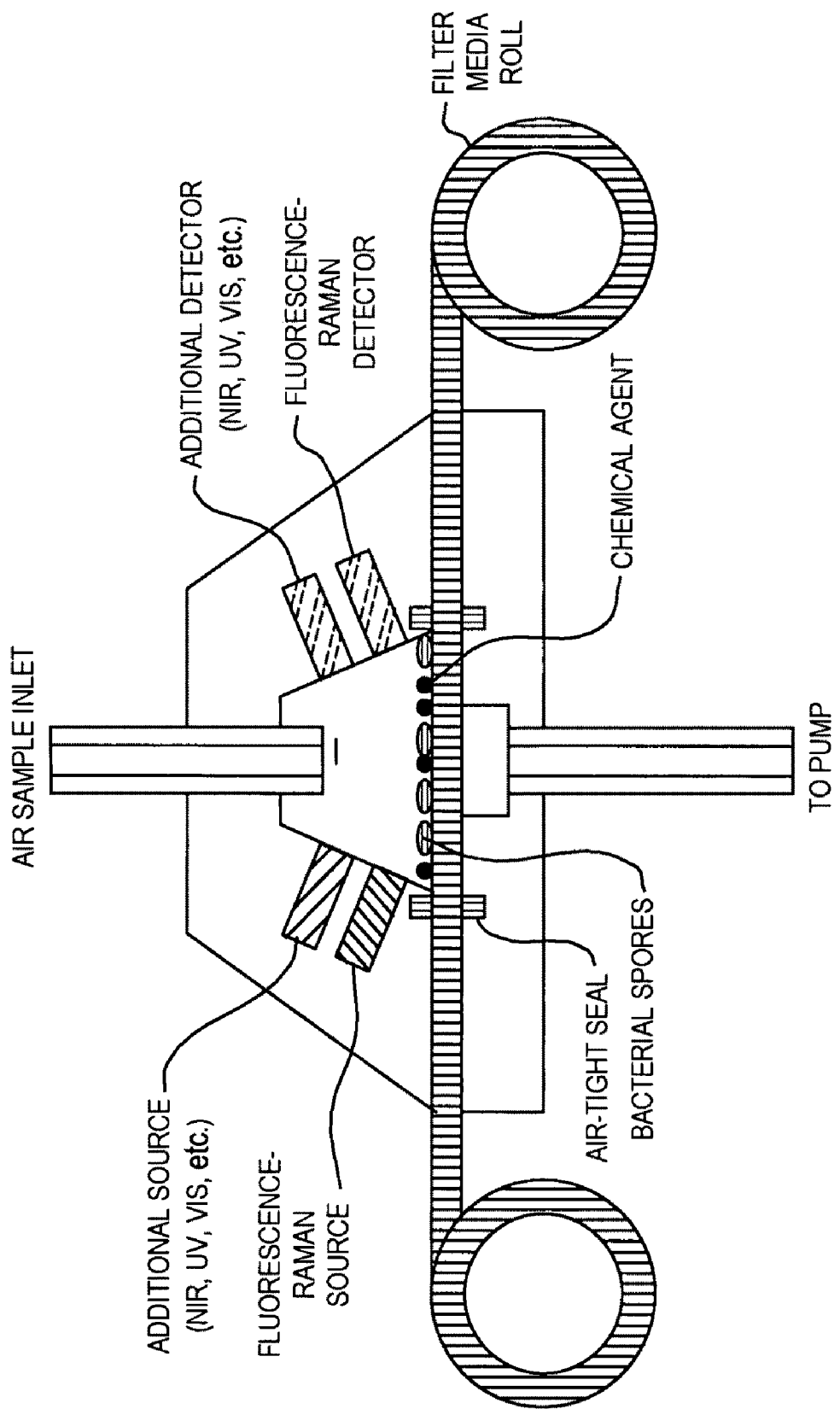
FIG. 2 is a schematic diagram of an ambient air sensor suitable for use in multimodal sensing and detection of BWA and CWA in systems described herein.

The invention includes an ambient air sensor system comprising two parts, a sampling system and a spectroscopic imaging system. The optics block of such a system is shown diagrammatically in FIG. 2. This block supports a section of a sample collection substrate such as a filter medium (e.g., a microporous filter medium having pores sufficiently small to substantially prevent passage of the hazardous agent of interest or a coated filter medium having pores large enough to permit passage of the hazardous agent of interest, but coated with an oil or other substance to which passing particles can adhere or into which passing molecules can be absorbed or dissolved) and provides an airtight seal around the periphery of the sampling area. This block should be easily opened so that either a new filter (when the system uses discrete filters as the substrate) or a new section of filter (when the system uses a continuous filter substrate) can be placed in the sampling/optics path. When a continuous substrate is used, a drive (e.g., a manual crank or a motor) can be included to advance the substrate between measurements, so that a fresh piece of the substrate is used for each measurement. The drive can be controlled by the same controller (or computer, if separate) used to control the optics.

The sampling system has an inlet, which is open to the atmosphere being tested. Its dimensions are optimized for the sampling flow rate and the anticipated range of particle sizes. For particulate or aerosol sampling, it is important that the inlet have no sharp bends or areas of low linear velocity, which can cause deposition of particulates prior to the collection filter. The sampling system includes or is connected to a sampling pump, which provides negative pressure to pull ambient air through the filter. Operation using positive pressure to force ambient air against the substrate is also possible. Air flow rates are in the range from 0.5 to 2.0 liters per minute are considered suitable for sampling, and a vacuum of about 100 inches of water (180 millimeters of mercury) should suffice to collect particulates in such a volume in a reasonable sample substrate area.

The sampling system can be operated continuously or, preferably, during a series of discrete sampling periods. At the end of each period, the sample collection substrate can be replaced (or advanced if a continuous medium is used). This can be done either by the operator or automatically. For continuous or interrupted sampling, the substrate can be in a tape-like filter configuration and new samples of filter can be positioned in the optics block by a tape-drive mechanism, similar to that of an audiocassette. A wide variety of appropriate sample collection medium are known, including filter media such as porous polypropylene media and aluminum media, in disk, sheet, and roll forms. Selection of an appropriate sample collection substrate is within the ken of a skilled artisan.

Once the particulates have been trapped on the sample collection substrate, multimodal spectroscopy is used to detect and classify the hazardous agent(s) present. If the excitation source is a laser which is coupled to the optics block using conventional or fiber optics to distribute the laser output over the sampling area, Raman imaging can be used. Alternately, the laser illumination can be shaped and/or split to match the distribution of points being selected (e.g., based on other optical properties of particulates on the substrate) or sampled. In another configuration, a light source comprised of a broadband UV/visible (UV/Vis), filtered UV/Vis, or a UV/Vis laser can be used to excite autofluorescence. The detector can be of the liquid crystal tunable type or another multi-point spectrometer type as described herein, and a CCD or other array camera can be used to define the sampling area at multiple wavelengths. Coupling of the detector to the optics block can be through fiber-based or conventional optics. The detector data is processed using chemometric and data analysis tools such as those in the CHEMANALYZE™ and CHEMIMAGE XPERT™ software packages.

The ambient air monitor can be operated intermittently, for example as a series of sampling periods during which periodic spectroscopic measurements are taken. The sampling periods can follow one another immediately (i.e., a subsequent sampling period begins immediately following the preceding sampling period) or be interrupted by a period of time (e.g., sampling periods interrupted by a 20 minute delay). The results from the previous and current sampling periods can interpreted by a system computer which can display results and activate warning and danger alarms, or initiate some action such as turning off a building outside air intake.

Figure 7A:
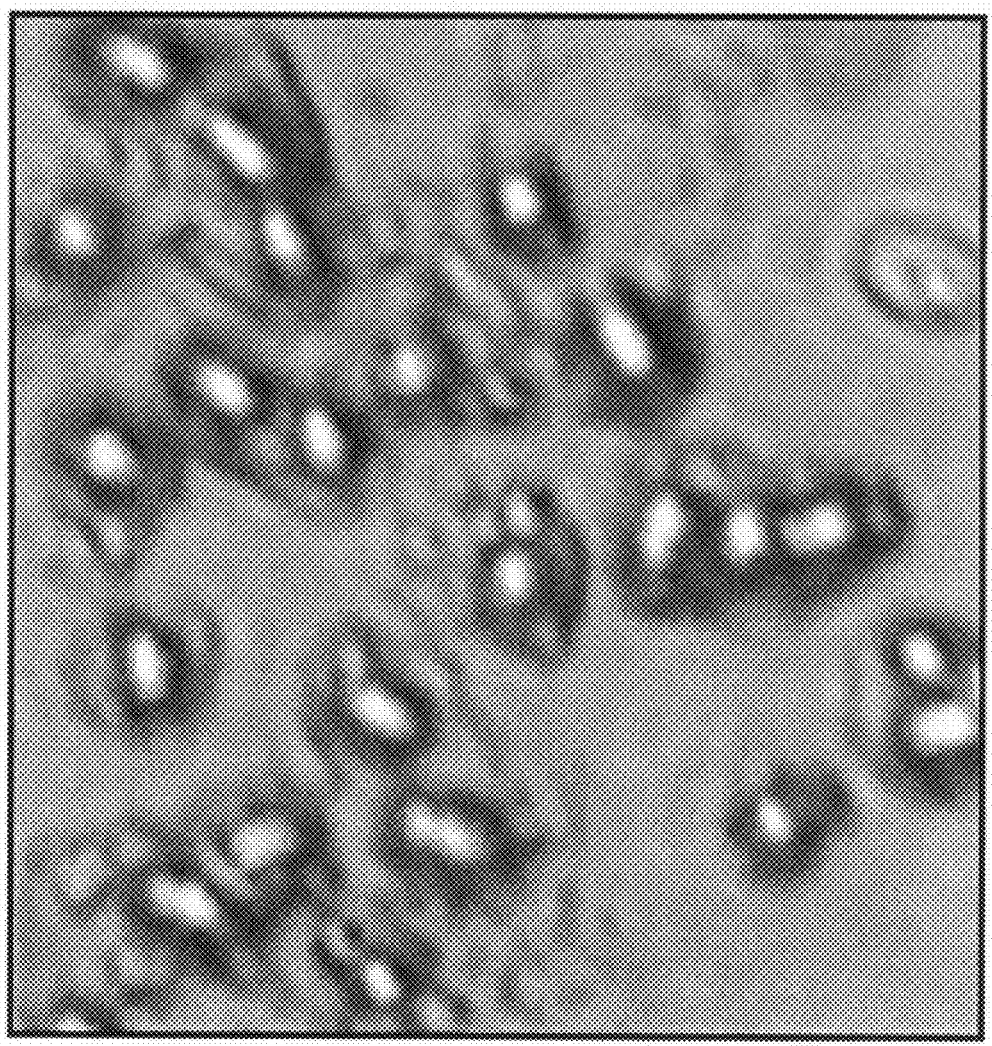
FIG. 7A is a brightfield optical reflectance microscopic image.
Figure 7B:
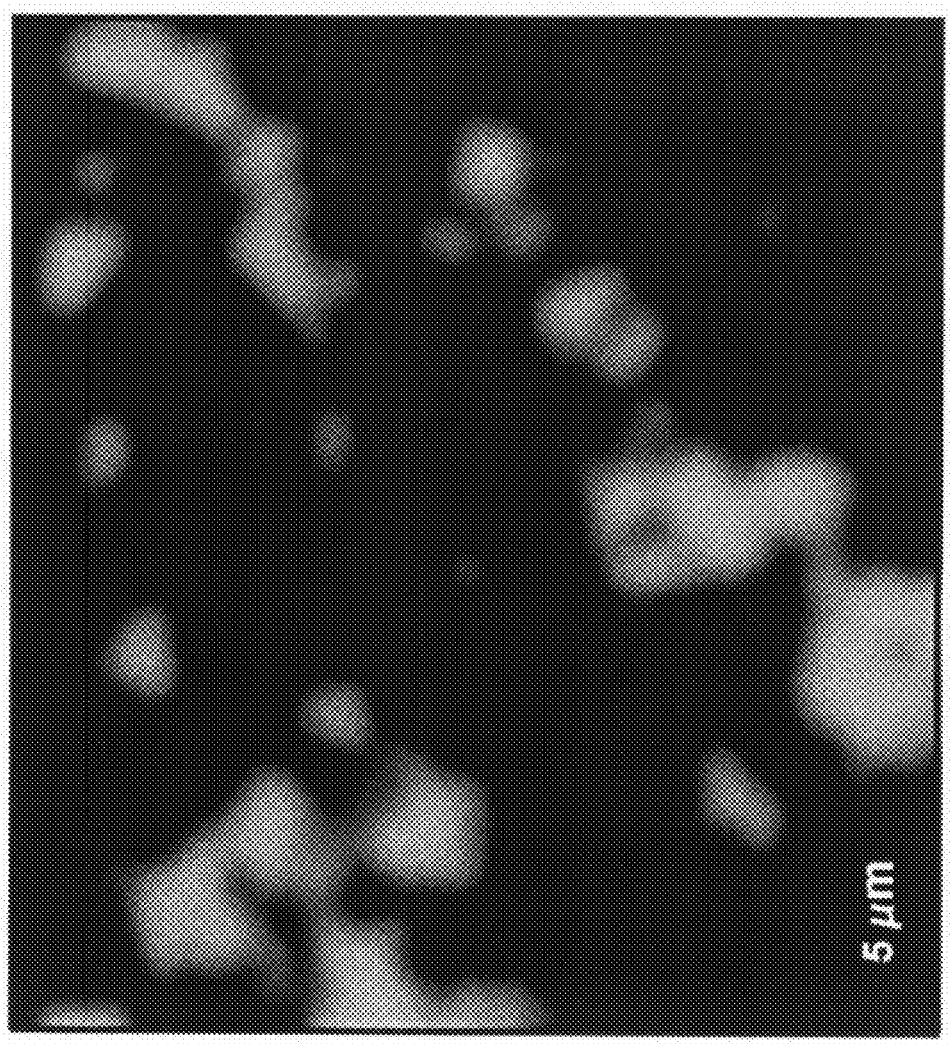
FIG. 7B is a Raman chemical image.
Figure 7C:
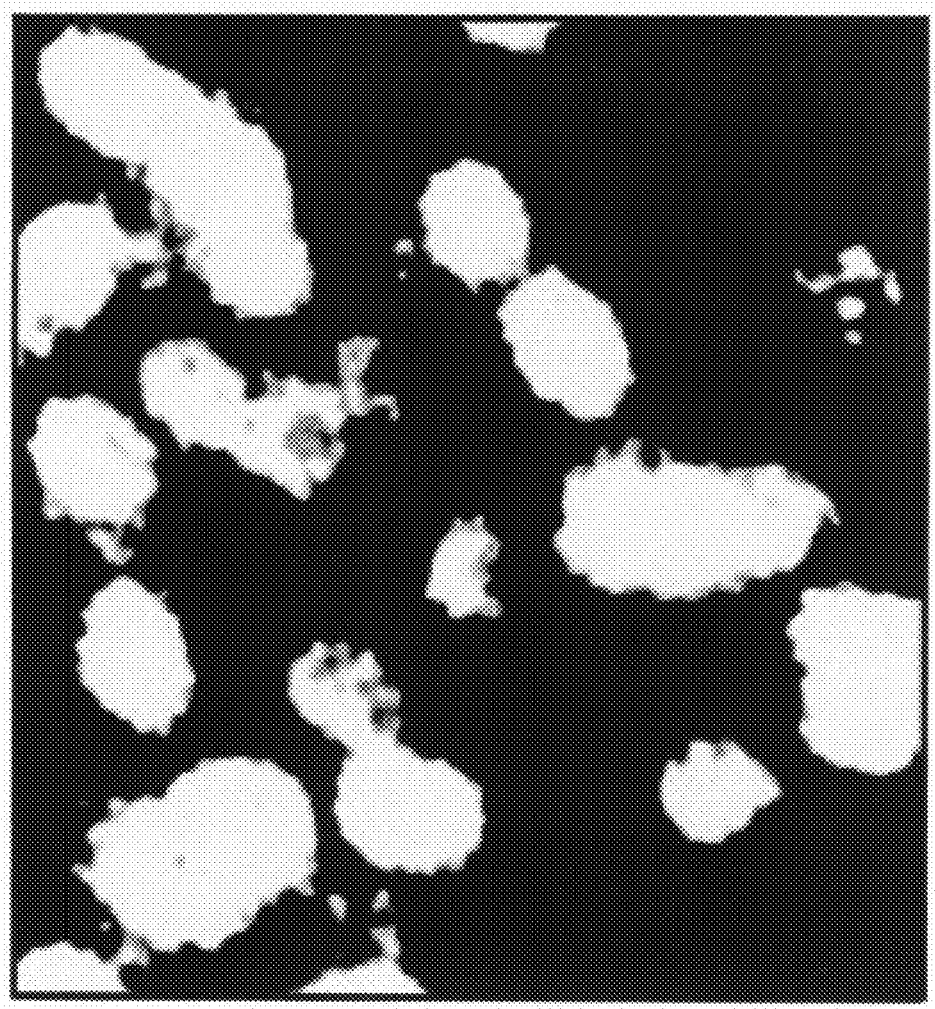
FIG. 7C is a fluorescent image of the field of view. In color FIGS. 7D and 7E, the brightfield image of FIG. 7A is combined with either (in FIG. 7D) the Raman chemical image of FIG. 7B or (in FIG. 7E) the fluorescent image of FIG. 7C.
Figure 7D:
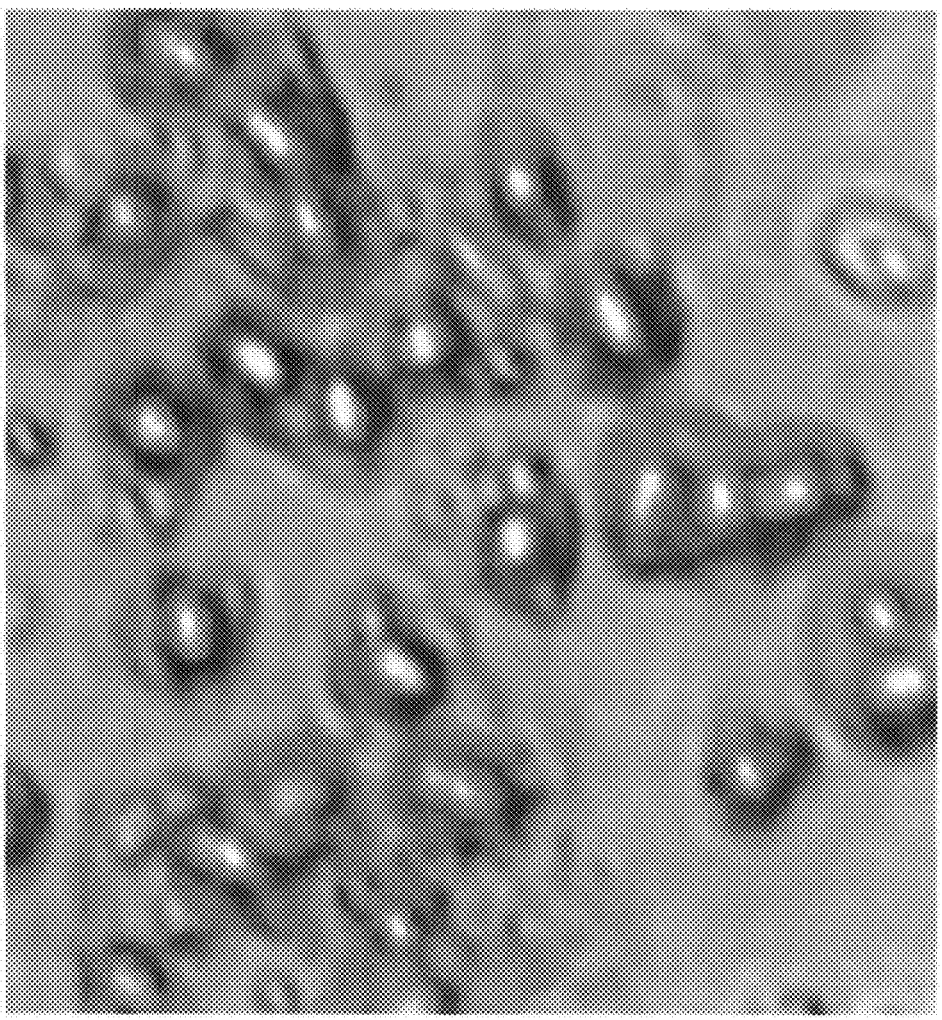
FIG. 7, consisting of FIGS. 7A, 7B, 7C, 7D, and 7E, depicts multimodal analysis of a single field of view of a mixture of *B. anthracis* with growth medium and formalin.
Figure 7E:
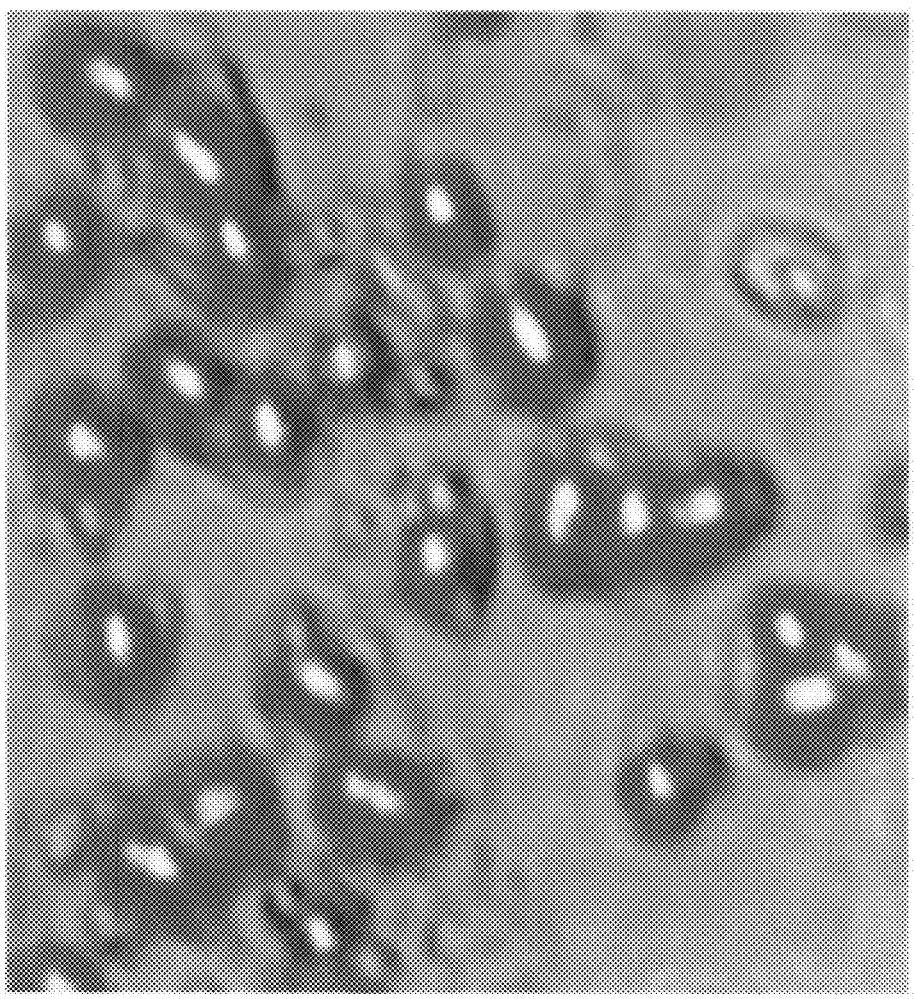
Figure 8A:
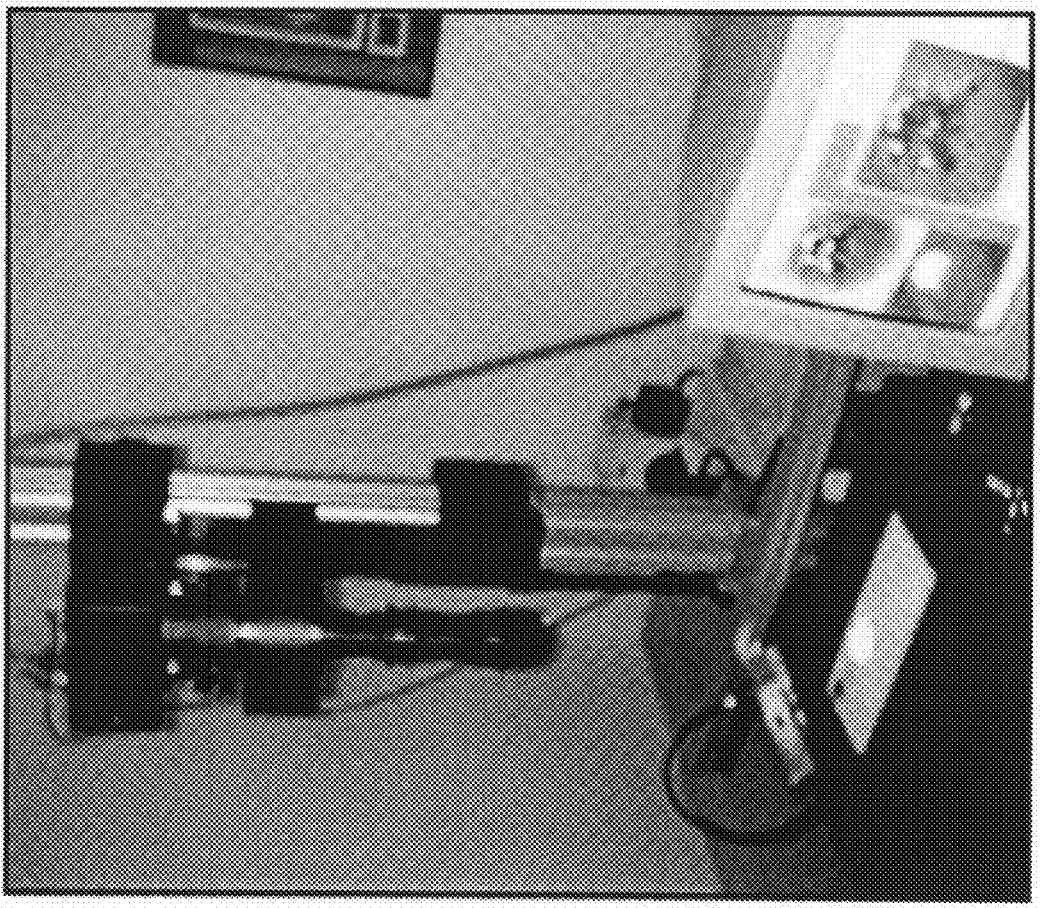
FIG. 8A depicts the configuration of the experiment.
Figure 8B:
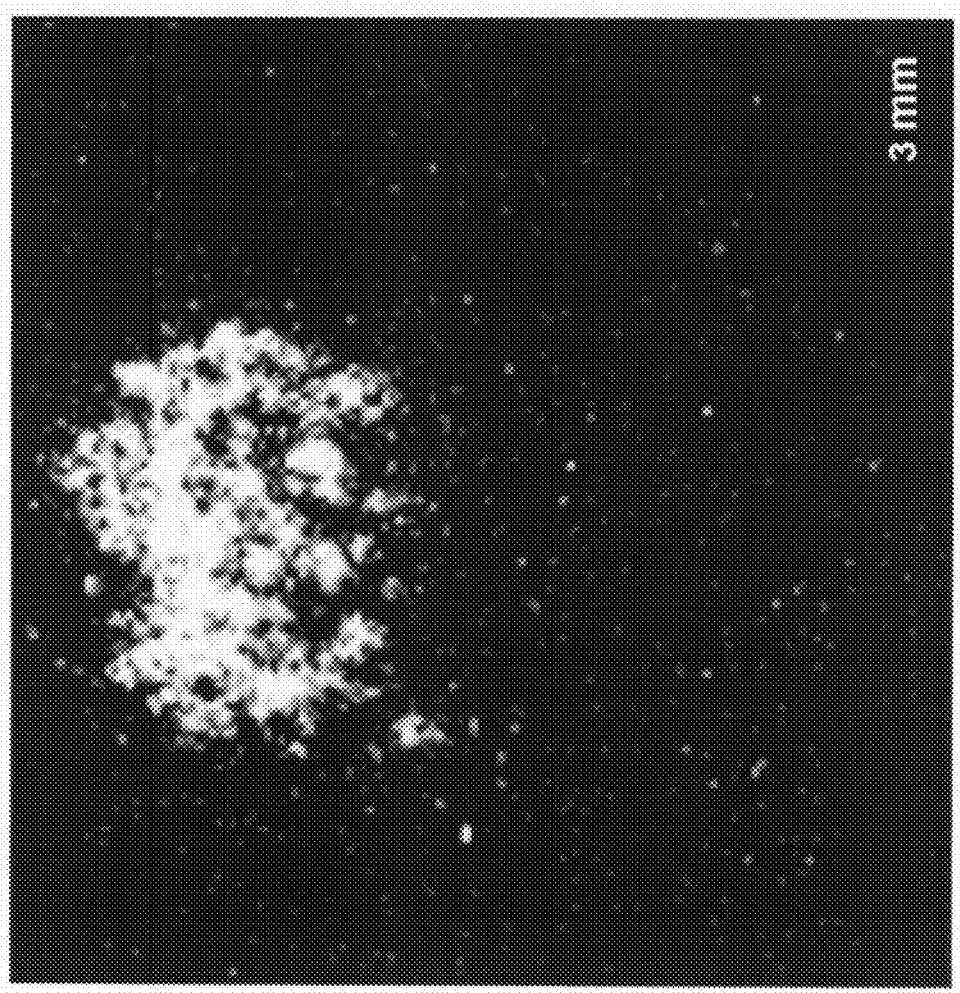
FIGS. 8B and 8C depict fluorescent images of *B. globigii* spores alone (FIG. 8B) and *B. globigii* mixed with baking soda (color FIG. 8C) on an envelope.
Figure 8C:
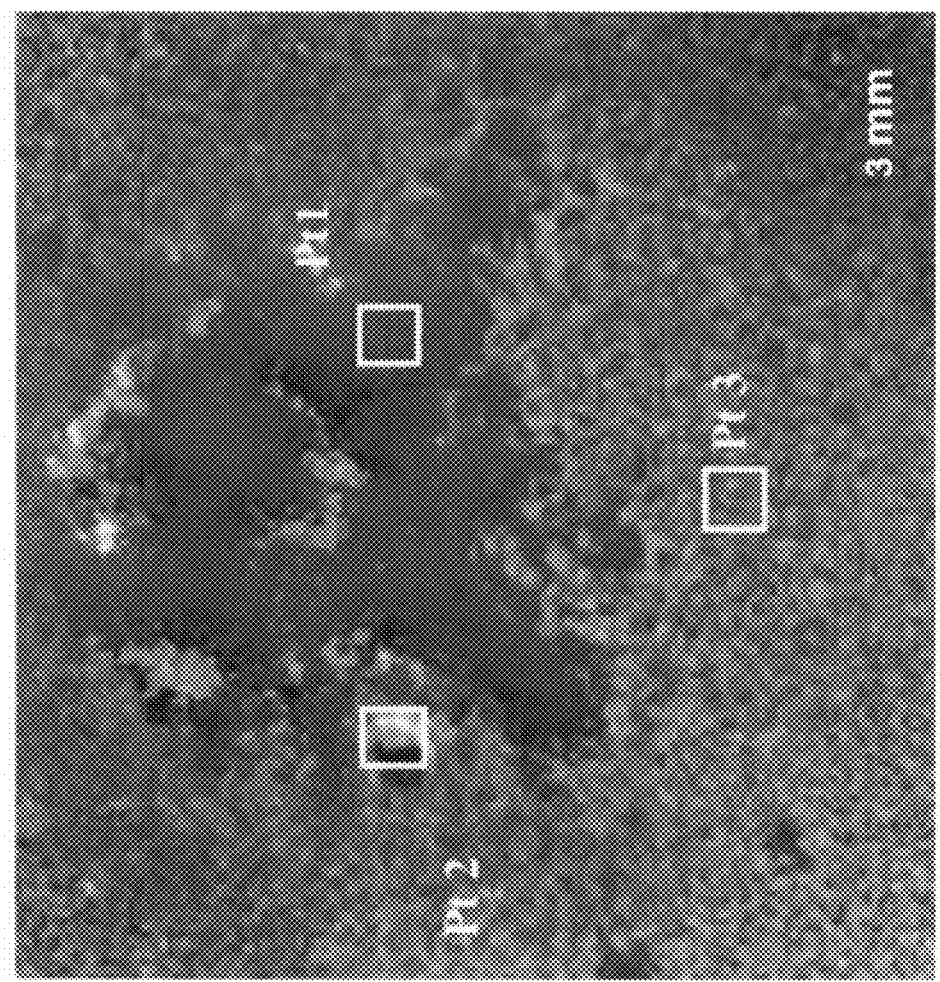
Figure 8D:
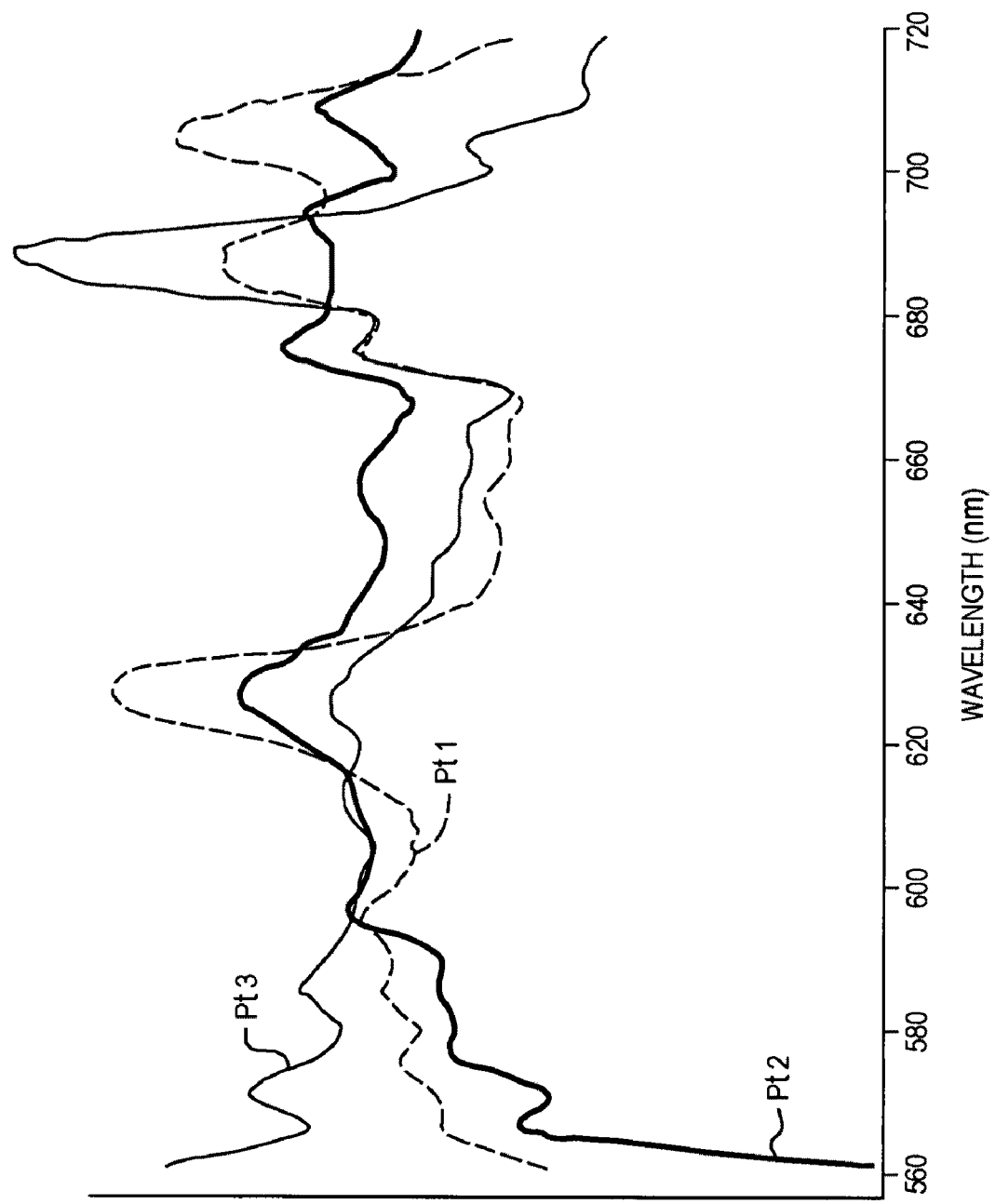
FIG. 8D depicts fluorescent spectral characteristic of baking soda (Pt1 in FIGS. 8C and 8D), *B. globigii* spores (Pt2 in FIGS. 8C and 8D), and the envelope (Pt3 in FIGS. 8C and 8D).

According to one embodiment of the disclosure, a detection apparatus comprises a Vapor Sniffer for continuous air monitoring and a Multipoint Raman Probe using fiber optics for liquid and solid detection. The handheld probe and Vapor Sniffer are integrated into a portable lightweight battery-operated backpack instrument. The backpack instrument houses the Vapor Sniffer along with the laser, spectrometer and computer, which are used to collect spectra that are gathered either through the Vapor Sniffer or the Multipoint Raman Probe. The computer reads the collected spectra and matches against a threat agent library. If a threat agent is detected, an audible alarm will sound and the result will display. Experimental Results are as follows:

Spectra generated using traditional spectroscopic methods can potentially reveal a wealth of information about molecular properties of hazardous agents. Spectroscopic imaging compounds this information by allowing variations in the composition of these materials to be probed downed to arbitrarily small levels (e.g., a single bacterium) if desired. FIG. 7, for example, shows an optical image (FIG. 7A), a Raman chemical image (FIG. 7B), and a fluorescent image (FIG. 7C) obtained from a mixture of *Bacillus anthracis* in a mixture medium components and formalin. FIGS. 7D and 7E are examples of image fusion of the optical image shown in FIG. 7A with the spectroscopic images shown in FIGS. 7B and 7C, respectively.

FIG. 4A depicts dispersive Raman spectra take from three different samples, each comprising one bacterial spore type. This demonstrates that despite the genetic and morphological similarities, Raman spectroscopy can be used to sufficiently discriminate among the different bacteria spores. The ability to distinguish the different spectra of small objects during one spectral scan is important for picking out and discriminating entities such as BWAs or CWAs in a mixture.

Figure 6A:
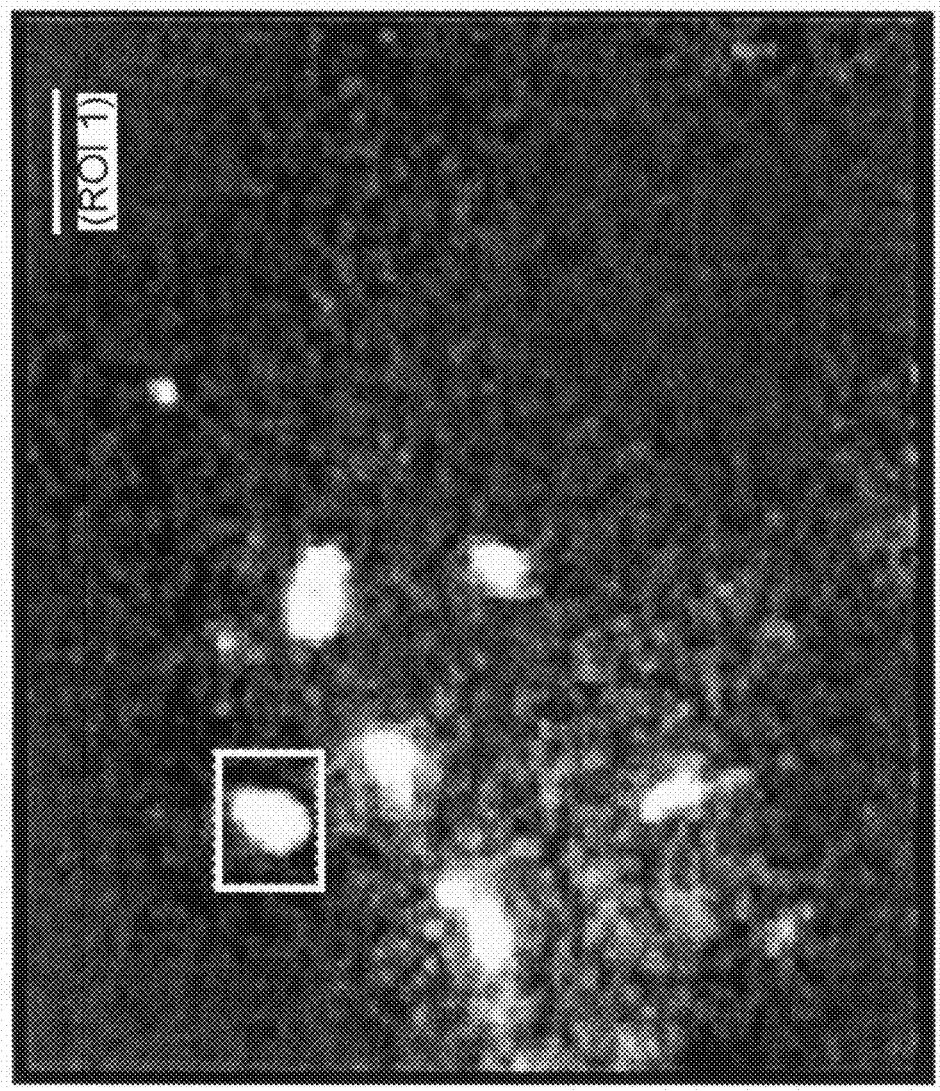
FIGS. 6A and 6B depict images of the same field of view of the mixture, assessed at different fluorescent wavelengths.
Figure 6B:
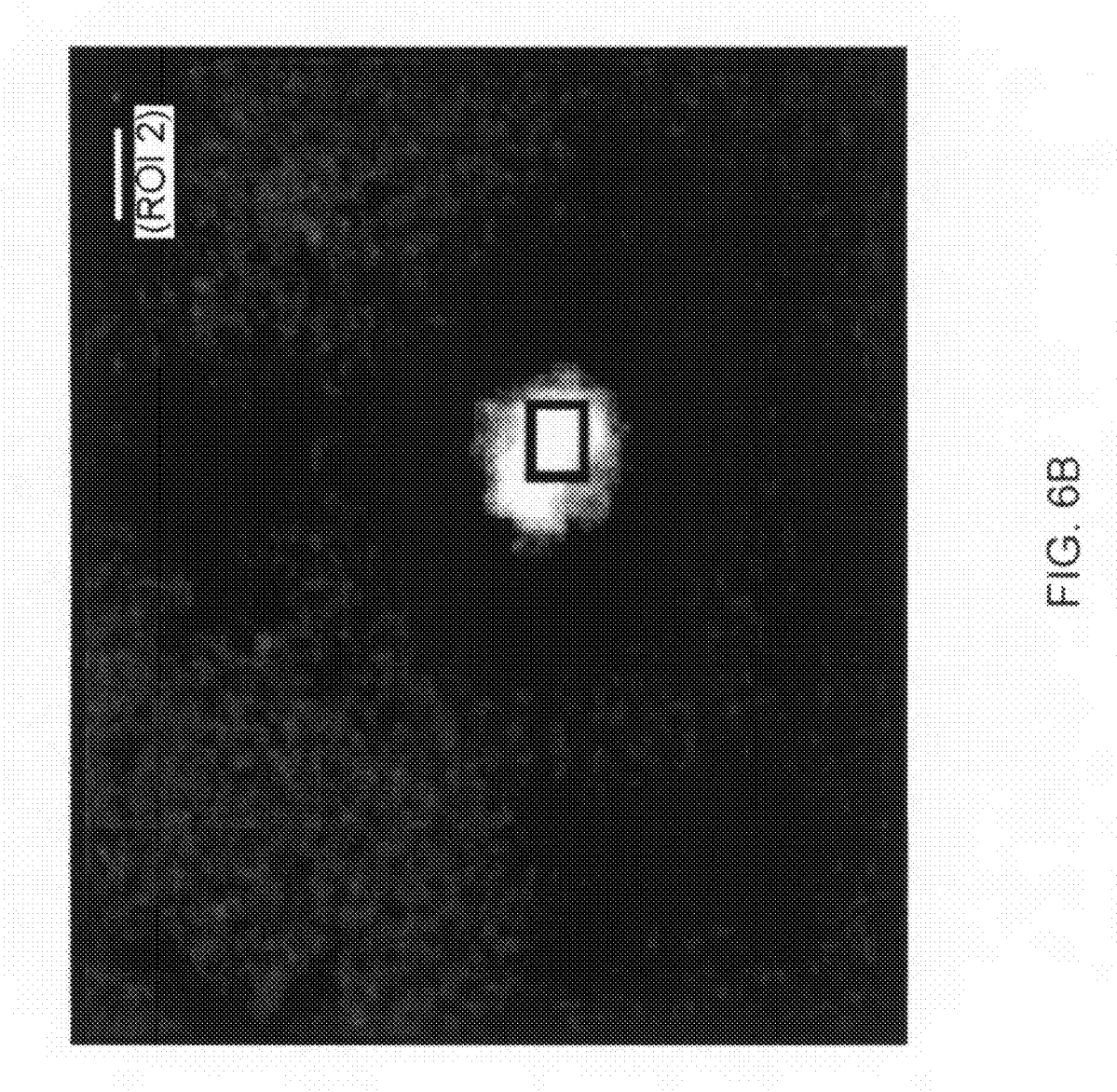
Figure 6C:
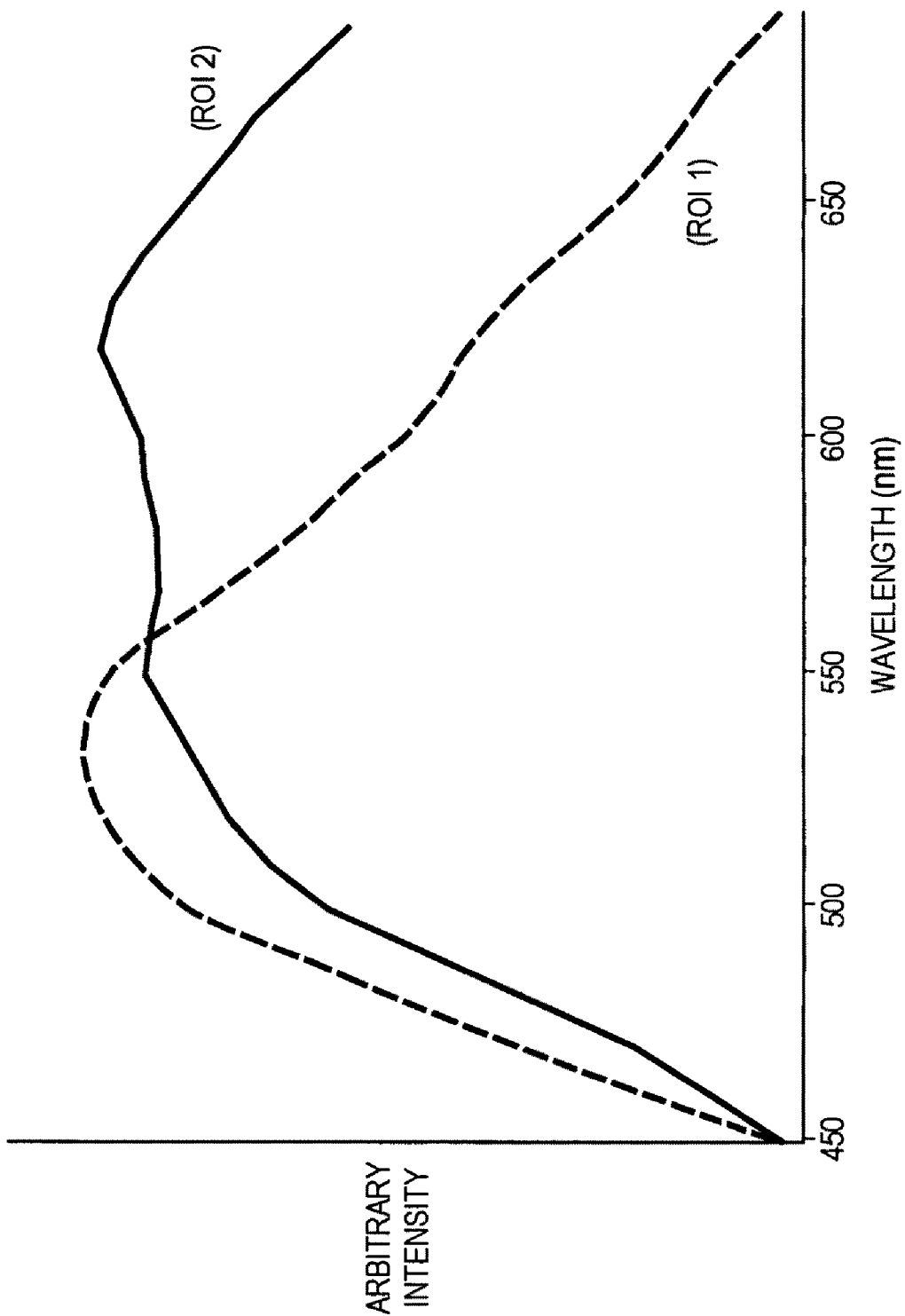
FIG. 6C depicts fluorescence spectra characteristic of *B. pumilus* (which fluoresces in FIG. 6A) and *B. subtilis* (which fluoresces in FIG. 6B).

FIG. 6 depicts how spectral sensing and analysis using a fluorescence system can also be used to discriminate and distinguish different *Bacillus* species. The fluorescence spectra in FIG. 6C were obtained for the two *Bacillus* types. Based on differences in these fluorescence spectra, particularly the peaks, *Bacillus subtilis* spores (which exhibit a fluorescence peak maximum at 630 nanometers) can be distinguished from *Bacillus pumilus* spores (which exhibit a fluorescence peak maximum at 540 nanometers). Images in FIGS. 6A and 6B depict the same microscopic field using different fluorescent spectral imaging wavelengths.

FIG. 8 depicts how fluorescent and visible spectral analysis in a macroscope system allows one to detect *B. globigii* candidate entities in a mixture of *B. globigii* and baking soda on the outside of an envelope. Raman spectral imaging of the sample areas (or one or more pixels within the areas) designated Pt1, Pt2, and Pt3 can be used to confirm the identities of the compounds identified by fluorescent spectrum in FIG. 8D by comparison with reference Raman spectra for those compounds.

Anthrax spores have been Raman imaged in a secure biohazard laboratory. Different strains of Anthrax spores have been differentiated by Raman spectroscopy and Raman imaging. Additionally, Raman spectral analysis of chemical images (i.e., Raman chemical imaging) has been used to differentiate same species and strain grown under different environmental conditions and/or growth medium. This ability can have useful investigatory applications. Similarly, Raman spectral analysis has been used to differentiate viable from non-viable endospores. Viability of suspect spores is a critical variable in determining the real threat posed.

Figure 5A:
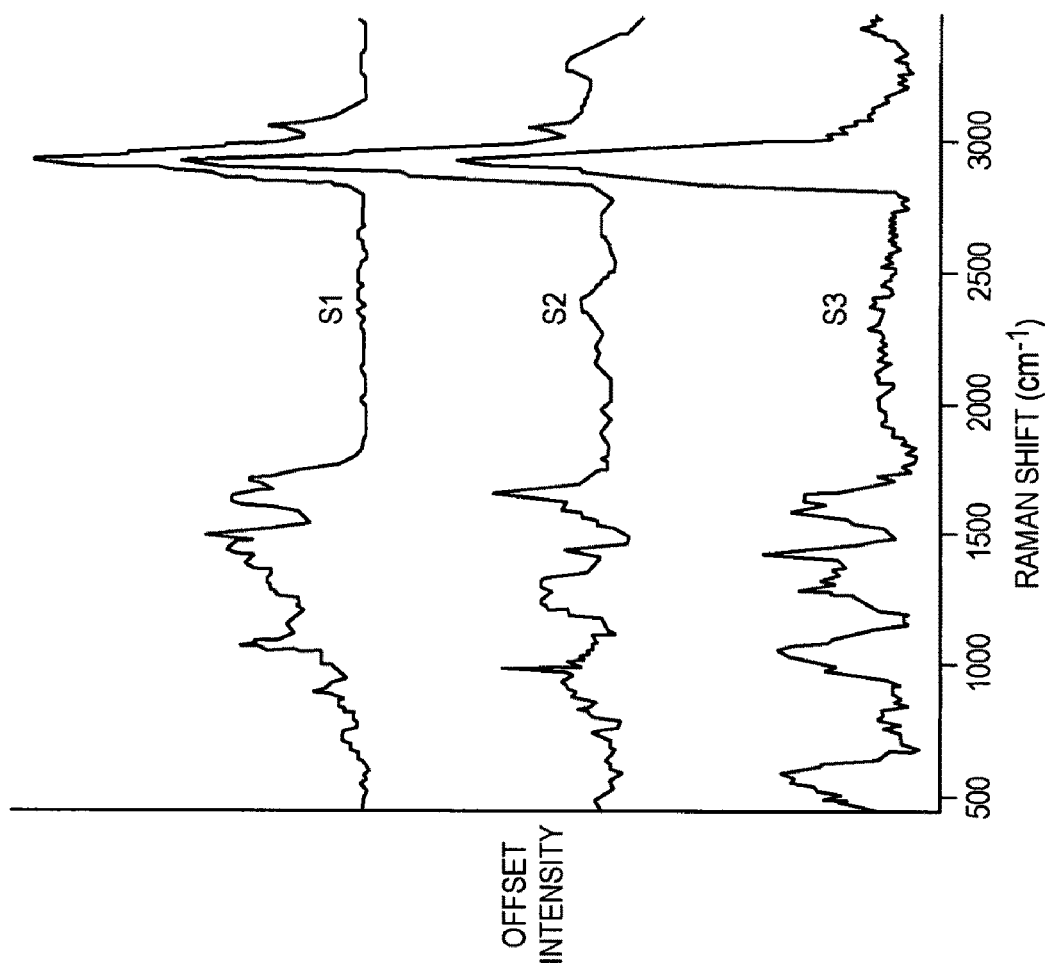
FIG. 5A depicts Raman spectra obtained by analysis of substances present in the sample imaged in the field of view depicted in FIG. 5B.
Figure 5B:
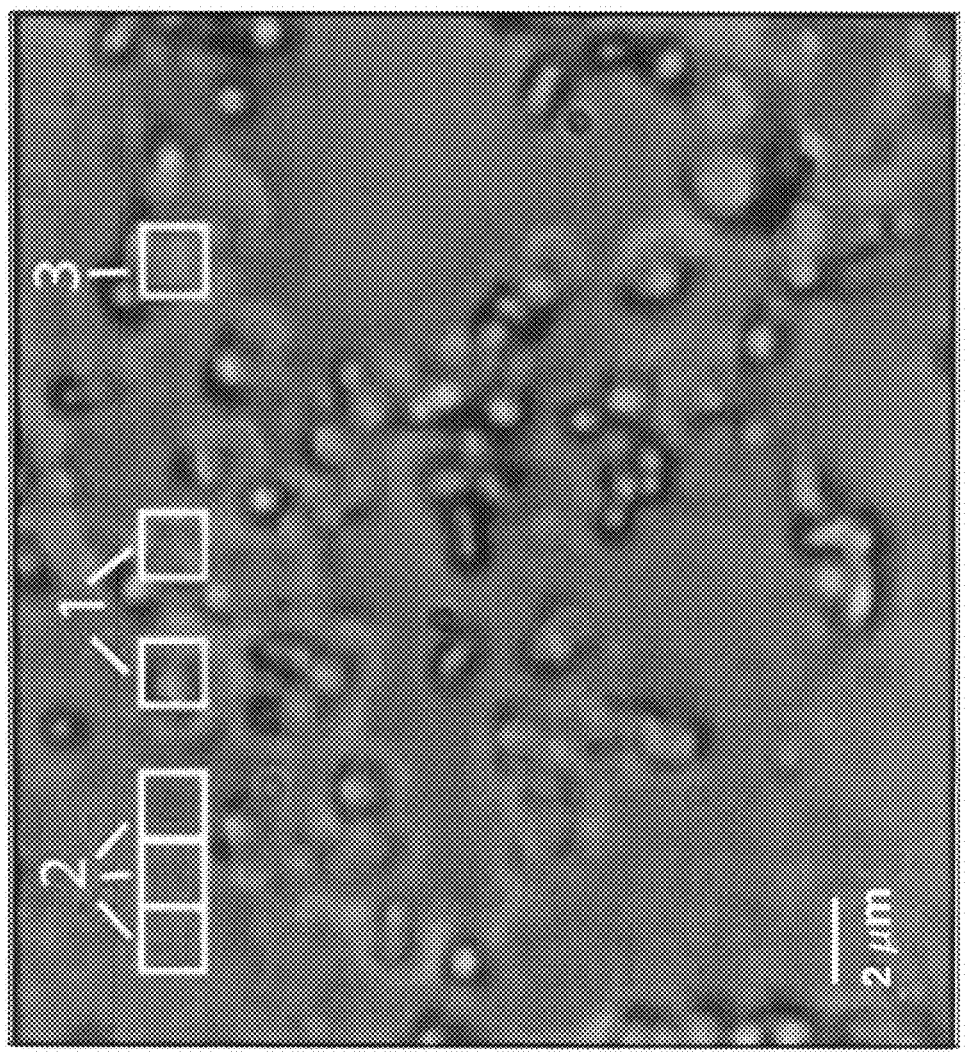
FIG. 5B is a color image of multiple entities in a microscopic field of view for a sample.
Figure 5C:
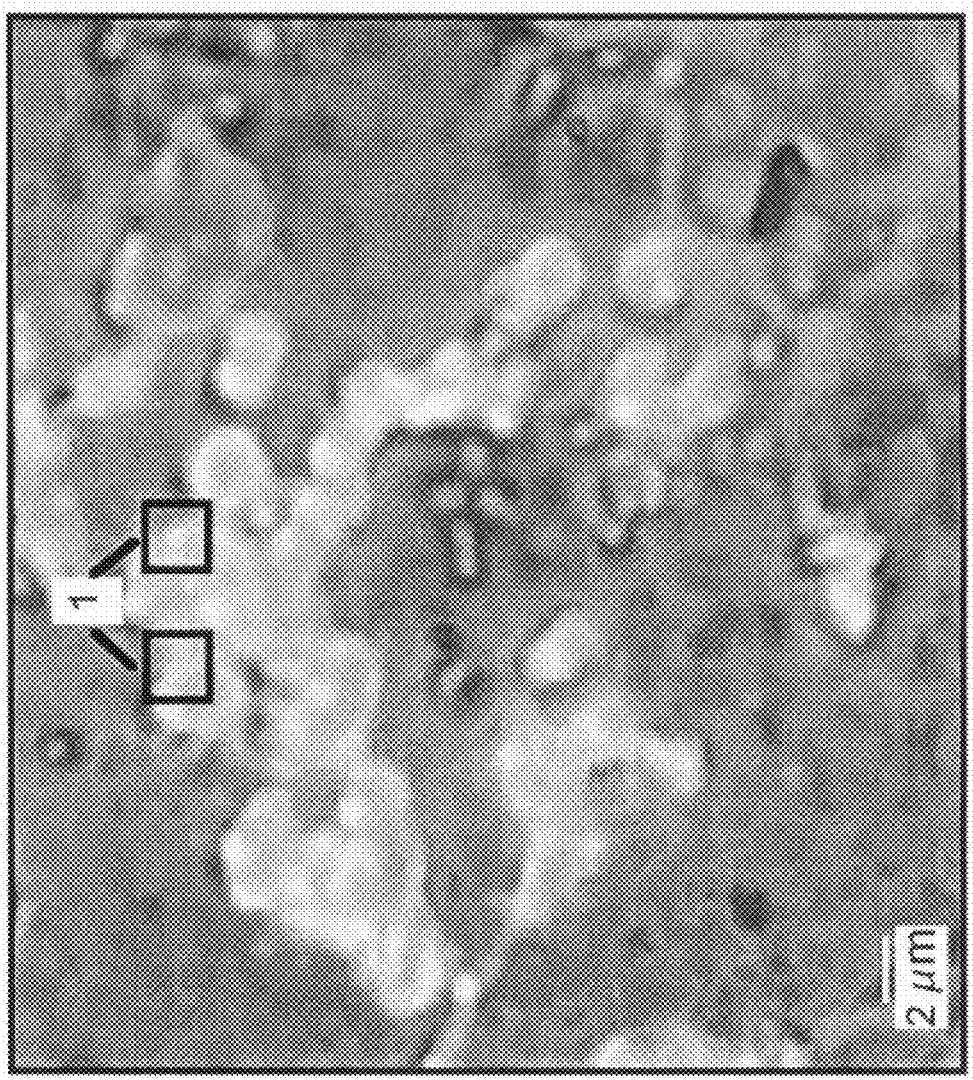
FIG. 5C is a monochrome image depicting Raman scattered radiation detected at an RS value of 2950 cm$^{-1}$ (±15 cm$^{-1}$).
Figure 5D:
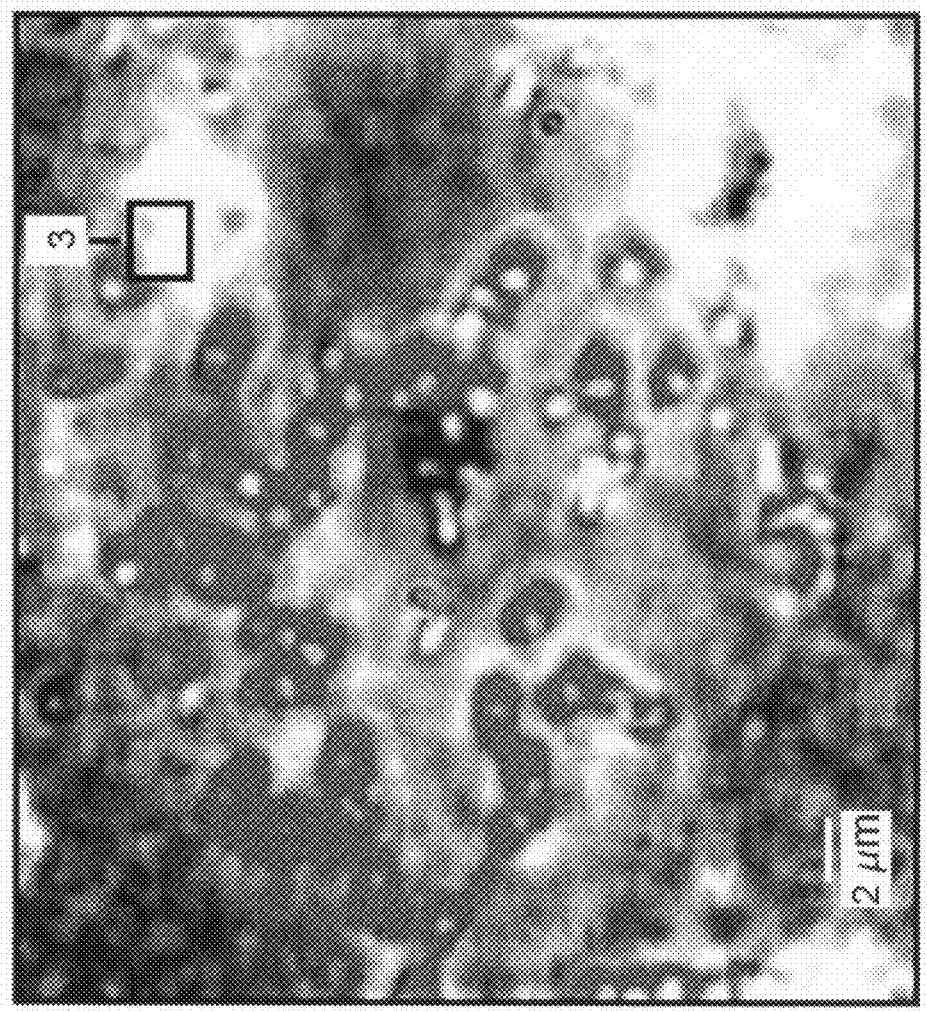
FIG. 5D is a monochrome image depicting Raman scattered radiation detected at an RS value of 3050 cm$^{-1}$ (±15 cm$^{-1}$).

The devices and methods described herein can be used to differentiate between multiple entities that may be present in a sample. FIG. 5B depicts an image of a sample comprising at least three different materials. FIG. 5A depicts Raman spectra of three components known to be present in the sample. Raman spectral analyses of the boxed portions of FIG. 5B indicate the identity of the entities within the boxes. These results demonstrate the capacity of the systems described herein for differentiating entities in a sample that are as diverse as *Bacillus* globigii (a bacterium), egg white (a protein agglomerate), and *Aspergillus terreus* spores (fungal spores). In FIG. 5B, *B. globigii* cells appear greenish, egg white appears reddish, and *A. terreus* spores appear bluish. In FIG. 5C, Raman scattered light having an RS value of about 2950 cm$^{-1}$ appears light-colored and corresponds with greenish areas in FIG. 5B, confirming occurrence of *B. globigii* cells in those portions of the field of view. In FIG. 5D, Raman scattered light having an RS value of about 3050 cm$^{-1}$ appears light-colored and corresponds with bluish areas in FIG. 5B, confirming occurrence of *A. terreus* spores in those portions of the field of view. The colors corresponding to selected RS values in composite images including Raman scattering and other spectroscopic data (e.g., composite images including Raman spectral data and visible light images, with or without fluorescent image data) can be the actual colors of Raman shifted light or pseudocolors. Pseudocolors can be selected to maximize contrast with other image components, to be consistent with pseudocolors used in separate images, to yield visually appealing images, or arbitrarily selected, for example.

A wide variety of biological pathogens can be detected using the multimodal spectral sensing methods described herein (i.e., for detection, classification as to species or strain, determination of viability, or some combination of these). These include eukaryotes such as protozoans and fungi (e.g., *Giardia* species, *Candida albicans*, or *Cryptosporidium* species in water or soil); bacteria (e.g., *Escherichia coli*, *Yersinia pestis*, *Francisella tularensis*, *Brucella* species, *Clostridium perfringens* and other species of *Clostridium*, *Burkholderia mallei*, *Burkholderia pseudomallei*, *Chlamydia psittaci*, *Coxiella burnetii*, *Rickettsia prowazekii*, *Vibrio* species, *Enterococcus faecalis*, *Staphylococcus epidermidis*, *Staphylococcus aureus*, *Enterobacter aerogenes*, *Corynebacterium diphtheriae*, *Pseudomonas aeruginosa*, *Acinetobacter calcoaceticus*, *Klebsiella pneumoniae*, *Serratia marcescens*); and viruses (variola, vaccinia, filoviruses such as Ebola and Marburg viruses, naviruses such as Lassa fever and Machupo viruses, and alphaviruses such as Venezuelan equine encephalitis, eastern equine encephalitis, and western equine encephalitis viruses). The methods can also be used to detect the causative agents of any viral, bacterial, parasitic, or prion disorder, including for example causative agents of disorders such as tularemia, brucellosis, glanders, melioidosis, psittacosis, Q fever, typhus, smallpox, and encephalitis.

In addition, just as toxic components in a masking mixture can be detected, so can specific materials in other mixtures be similarly determined. These includes but is not limited to a wide range of mixtures such as hazardous agents in blood, impurities or active ingredients in drug tablets, and specific entities among airborne particulates.

Data Analysis

Data analysis and chemometric tools examine the differences in fluorescence or Raman spectra found for each of the spectra and perform a separation into principal components to distinguish the pure components and identify the respective component, for example by comparison with a reference database of spectra stored in data storage entity 430 of FIG. 1. Methods of comparing a Raman spectrum with one or more reference spectra are known in the art.

A variety of data processing procedures can be used with these systems. For example, a weighted multi-point spectral data subtraction routine can be used to suppress contribution from the sample background or sample support (e.g., Raman light scattered by a microscope slide). Alternatively, multivariate spectral analysis involving principal factor analysis and subsequent factor rotation can be used for differentiation of pure molecular features in hazardous agents, and other entities (e.g., non-threatening 'masking' compounds).

The following is an example of an algorithm that can be used to perform this multi-point analysis, and uses a mixture of *Bacillus subtilis* and *B. pumilus* spores as a sample:

1. Load a fluorescence image from stored values or from an instrument output.
2. Load a brightfield microscope image of the same field of view from stored values or from an instrument output.
3. Perform instrument response correction by dividing each image by a calibration image.
4. Pre-process both images to remove outliers and noise, for example using 4a. A cosmic filter to achieve median filtering for points whose values differ significantly from the local neighborhood mean and 4b. A Wiener filter to achieve spatial image smoothing to remove additive noise.
5. Using the brightfield image, obtain a binary mask of the spores using one of several possible methods, two of which are:

5a. Watershed segmentation, which marks each spore and segments each spore based on the gradient of its' intensity profile, and 5b. Otsu thresholding method to determine an optimum intensity threshold (See Otsu, 1979, "A Threshold Selection Method from Gray-Level Histograms," IEEE Transactions on Systems, Man, and Cybernetics 9(1):62-66)
6. Perform particle analysis on the binary objects to obtain spatial features such as area, length, width, shape factor, eccentricity, and the like.
7. Multiply the fluorescence image by the binary mask.
8. Perform principal component analysis (PCA) on this masked fluorescence image to obtain the most significant principal components and corresponding score images that comprise a certain majority percentage of the variance. For instance, if two principal components comprise 99% of the variance, and 99% is the specified threshold, two score images are retained.
9. Create "spectral" features from the average of the score images over the pixels comprising the masked objects.
10. Combine the spectral and spatial feature vectors.
11. Perform PCA on the combined feature vectors.
12. Cluster the PCs with multidimensional k-means clustering, with the number of clusters specified by the number of PCs retained in Step 8.
13. Assign each cluster a color, and assign the corresponding color to the objects in the mask. This color image shows the detected threats.
14. Perform image fusion to correlate features with the optical or other image features which have been characterized by other methods.

Applications

The devices, systems, and methods described herein are suitable for rapid (chemical and/or biological) detection of hazardous agents and other applications. Configured in the macroscopic version of the technology, multimodal spectroscopic sensing can be employed for rapid assessment of large areas for suspect hazardous agents based on their fluorescence, NIR, UV/visible properties, or on some combination of these properties. Configured in the microscopic mode, visualization, positive detection, classification, and identification of suspect hazardous agents can be made. Configured in the endoscopic mode, hazardous agents can be visualized, detected, classified, and identified remotely. Configured in FAST mode, hazardous agents can be detected, classified, identified, and visualized remotely or at the microscope in real-time. When configured as an air sampler, unambiguous detection of airborne hazardous agents can be performed.

Advantages Over Currently Available Technology

Traditional approaches to detection of hazardous biological agents include inoculation methods, enzyme-linked immunosorbent assay (ELISA) methods, BIOTHREAT ALERT (TM, Tetracore Inc, Gaithersburg, Md.; BTA) test strips, DNA-based tests, DNA chip analyses, and mass spectrometry.

Inoculation methods involve the inoculation of suspect culture or specimen into an animal that is then observed for development of disease. In addition to animal cruelty issues, there are drawbacks with this approach including the extensive amount of time required to achieve detection.

ELISA tests involve antibody detection. This technique is also slow and suffers from a high rate of false positive results (e.g., unrelated antibody reacts with antigen nonspecifically) and false negative results (e.g., interfering compounds present in blood or antibodies not concentrated enough to be detected). Furthermore, a patient can test positive to antibodies long after the patient has recovered.

BTA test strips are small plastic devices that work very much like a home pregnancy test. The test strips contain specific antibodies that change color on the strip indicating the presence of a bio-threat agent. A negative result means the bio-threat agent is not present within the detection limit of the strip. Although results can be obtained in a relatively short period (e.g., 15 minutes), the incidence of false negatives and false positives is high.

DNA-based tests detect biological agents by recognizing their genetic sequences. While more sensitive than BTA test strips, DNA-based tests are susceptible to masking agents and involve a lengthy analysis time. DNA chip analysis involves the immobilization of DNA strands on a Si or glass wafer chip. DNA will bind to or hybridize complementary DNA strands in the sample being tested. A specially designed microscope detects where the DNA hybridizes. Amplification is achieved by polymerase chain reaction (PCR). Detection of bio-threat agent is reported to be possible within minutes. The limitations of DNA-based methods are two-fold. First, DNA methods are designed to detect a specific bio-threat agent through its unique DNA sequences. Therefore, each DNA test is specific to one agent and if it is desired to detect additional agents, additional test reagents must be developed. A second limitation revolves to the problems of false negatives and false positives due to environmental contamination. DNA tests are well known to have problems yielding correct results in "real-world" samples.

Mass Spectrometry (MS) uses the pattern of mass fragments generated when a cell, spore, or chemical is subjected to an ionization process under high vacuum to characterize the organism(s) or chemical(s) present in a sample. This technique has the advantage of very sensitive detection, but requires a sophisticated sampling system in order to deliver a representative sample to the ionizer. The main limitation of MS is that it requires the use of high vacuum pumps that are inherently delicate and expensive. An additional limitation is that it is a destructive technique.

Alternative embodiments of the devices and systems described herein include probes or microscopes based on spectroscopic methods including Raman, fluorescence, NIR, and others for rapid, non-contact, and accurate detection of hazardous agents. Similar techniques have been previously applied in a time-consuming approach involving spectroscopically addressing individual points in a sample, one at a time. The multimodal spectral sensing methods described herein rapidly provide data needed for automated spectral analytical methods. Partial component analysis approaches can be used in combination with these methods for chemical imaging analysis. The multimodal spectral sensing methodology described herein can be implemented in a miniaturized, compact sensing platform. The devices, systems, and methods described herein can be used to identify the distribution of individual hazardous agents in the presence of other hazardous agents, environmental contaminants, and/or non-threatening 'masking' agents, in either local and remote environments. These are characteristics that no traditional method provides. The devices, systems, and methods described herein can exhibit a lower incidence of false positive and false negative results, and permit one to determine if a true threat exists in a time frame of minutes.

Trimodal Chemical Imaging of Fluorescein-5-Isothiocyanate (FITC)

Integrated fluorescence imaging of cells is a well-established technology in the field of fluorescence-based cell and molecular biochemical assays. In particular, this method is widely used for detection of drug-cell interactions as part of drug discovery and development. This type of imaging is generally carried out using bandpass optical filters, and in so doing provides no information regarding changes in band shape or peak position related to the chemical environment or interactions of the molecular probes. In contrast, hyperspectral fluorescence imaging provides spectra associated with each pixel of the image, thereby revealing information about the chemical environment and molecular interactions at each spatial location in the field of view. Additional hyperspectral modalities that can be applied to that same field of view include visible absorption and Raman imaging. The probing of chemical interactions through the combination of electronic and vibrational modes of spectroscopic imaging from the same field of view provides a wealth of information regarding biological systems such as cells, tissues, and organisms.

Three-mode chemical imaging, based on assessment of visible absorption, fluorescence emission, and Raman scattering, can be performed using a single instrument. The instrument includes a liquid crystal tunable filter (LCTF) and a charge-coupled device (CCD) imaging camera as described herein. This instrument can be used to perform three modes of spectral imaging of solvated compounds, such as those commonly used as molecular probes for bioimaging applications.

To understand the chemical basis, consider the widely used molecular probe, FITC (molecular formula: $C_{21}H_{11}NO_5S$, molecular weight: 389.38). FITC is an exogenous fluorophore—that is, a molecule that must be conjugated to a biomolecule to function as a fluorescent tag that achieves specificity with respect to certain biological sites. A feature common to exogenous fluorophores is their highly conjugated chemical bonding from which arise the electronic transitions associated with strong absorptions of visible light and subsequent emissions, often at high quantum efficiency. Also, the highly conjugated pi-bonding contributes to the high polarizability of the molecule, which also contributes to strong Raman scattering attributable to vibrational transitions. Consequently, the molecular structure of exogenous fluorophores is ideal for the development of multimode hyperspectral imaging.

Figure 9:
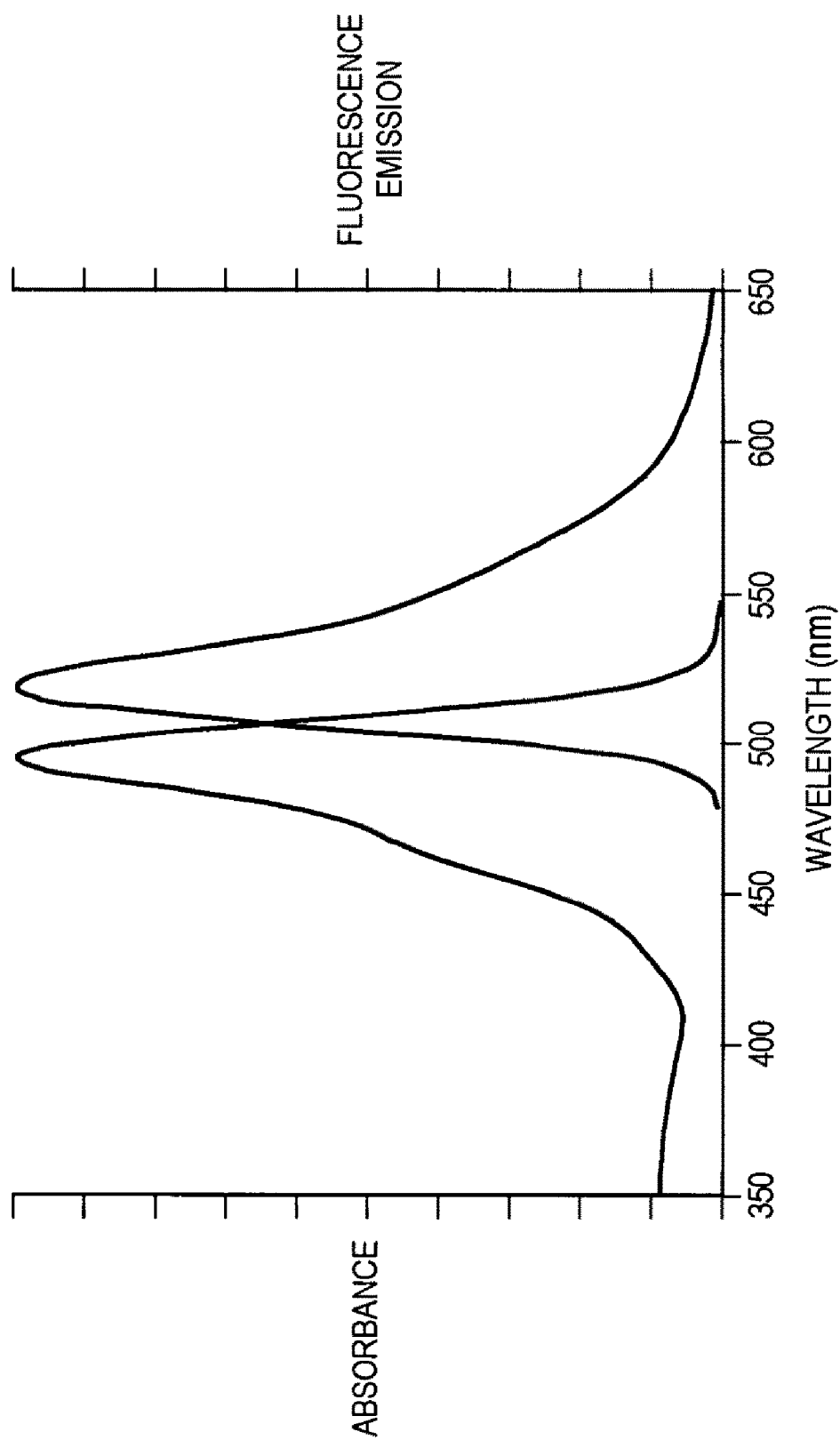
FIG. 9 is the absorbance and fluorescence emission spectra of goat anti-mouse IgG labeled with FITC in pH 8.0 buffer.

The absorption and fluorescence emission spectra of FITC are shown in FIG. 9. FITC absorbs light at wavelengths between 425 and 525 nanometers, and manifests an absorption maximum at approximately 490 nanometers. The fluorescence emission manifests a modest Stokes shift (energy difference between the absorption and emission maxima) with an emission maximum at approximately 520 nanometers. Therefore, a hyperspectral fluorescence image can be produced by irradiating a sample containing FITC with light having a wavelength of 488 nanometers (e.g., the 488 nanometer line of an argon laser). Hyperspectral Raman images can be generated by irradiating the sample with either a 632.8 nanometer line from a He—Ne laser or the 635 nanometer line from a semiconductor laser. Either red wavelength is significantly longer than either the absorption or emission maxima, and no fluorescence would be expected to interfere with Raman scattered radiation upon Raman imaging of a sample illuminated with these red wavelengths. Consequently, hyperspectral Raman and fluorescence images can be obtained from the same field of view of a sample containing FITC by proper selection of the illumination wavelengths.

Hyperspectral absorption images can be generated by transmitting white light through the sample and passing it through the LCTF and focusing the light on a CCD imaging camera. The light collection, wavelength selection, and imaging camera can be the same for hyperspectral absorption, fluorescence emission, and Raman imaging. Consequently, all three modes of hyperspectral imaging provide complementary chemical information about the exact same locations in a single field of view.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of assessing occurrence of a pathogen in a sample that comprises multiple entities, the method comprising assessing a first optical property of the entities, wherein the first optical property is characteristic of the pathogen, selecting only an entity exhibiting the first optical property and thereafter performing an assessment of Raman-shifted radiation scattered by the selected entity, wherein one or more entities failing to exhibit said first optical property are excluded from said assessment wherein exhibition of a Raman scattering property characteristic of the pathogen by the selected entity is indicative that the pathogen occurs in the sample.

2. The method of claim 1, wherein the first optical property is selected from the group consisting of absorbance, fluorescence, diffraction, polarization, microscopic morphology, and an optical property associated with particle motion.

3. The method of claim 1, wherein the first optical property is microscopic morphology.

4. The method of claim 3, wherein the morphology is assessed by a method selected from the group consisting of scanning electron microscopy, visible light reflectance microscopy, ultraviolet light reflectance microscopy, light reflectance microscopy, visible light transmission microscopy, ultraviolet light transmission microscopy, infrared light transmission microscopy, and fluorescence microscopy.

5. The method of claim 4, wherein the morphology is assessed by visible light reflectance microscopy.

6. The method of claim 1, comprising assessing Raman-shifted radiation scattered by a selected entity that also exhibits a second optical property characteristic of the pathogen.

7. The method of claim 6, wherein the second optical property is selected from the group consisting of absorbance, fluorescence, diffraction, polarization, and microscopic morphology.

8. The method of claim 6, wherein Raman-shifted scattered radiation is assessed only for entities for which the first and second optical properties are characteristic of the pathogen.

9. The method of claim 6, wherein the first optical property is microscopic morphology.

10. The method of claim 9, wherein the second optical property is fluorescence.

11. The method of claim 10, wherein the first and second optical properties are both assessed by fluorescence microscopy.

12. The method of claim 10, wherein the morphology is assessed by visible light reflectance microscopy.

13. The method of claim 10, wherein fluorescence is assessed only for entities that exhibit microscopic morphology characteristic of the pathogen.

14. The method of claim 1, wherein the pathogen is a synthetic organic chemical.

15. The method of claim 1, wherein the pathogen is an inorganic chemical.

16. The method of claim 1, wherein the pathogen is a biological toxin.

17. The method of claim 1, wherein the pathogen is a microorganism.

18. The method of claim 17, wherein the microorganism is a bacterium.

19. The method of claim 17, wherein the microorganism is a protozoan.

20. The method of claim 1, wherein the pathogen is a virus.

21. The method of claim 1, wherein the Raman-shifted scattered radiation is transmitted through a filter prior to assessing the Raman-shifted scattered radiation.

22. The method of claim 21, wherein the filter is selected from the group consisting of a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter.

23. The method of claim 1, wherein the Raman-shifted scattered radiation is transmitted through an interferometer prior to assessing the Raman-shifted scattered radiation.

24. The method of claim 23, wherein the interferometer is selected from the group consisting of a polarization-independent imaging interferometer, a Michelson interferometer, a Sagnac interferometer, a Twynam-Green interferometer, a Mach-Zehnder interferometer, and a tunable Fabry Perot Interferometer.

25. The method of claim 1, wherein the Raman-shifted scattered radiation is collected using a device selected from the group consisting of a macroscope, a microscope, an endoscope, and a fiber optic array.

26. The method of claim 1, comprising assessing a Raman scattering spectrum of the selected entity.

27. The method of claim 26, wherein the spectrum includes Raman shift values in the range 20-2000 $cm^{-1}$.

28. The method of claim 26, wherein the spectrum includes Raman shift values in the range 2700-3200 $cm^{-1}$.

29. The method of claim 26, wherein the spectrum includes Raman shift values in the range 1000-2000 $cm^{-1}$.

30. The method of claim 26, wherein the spectrum includes Raman shift values in the range 500-3000 $cm^{-1}$.

31. A device for assessing occurrence of a pathogen in a sample that comprises multiple entities, the device comprising a radiation source for irradiating the sample, a detector for detecting an optical property of the entities, a Raman detector for detecting Raman-shifted radiation scattered by the entities, and a controller operably linked to the Raman detector wherein said controller restricts detection of Raman-shifted radiation only to entities for which the optical property is characteristic of the pathogen.

32. A device for assessing occurrence of a pathogen in an ambient sample, the device comprising an air handling system for depositing particles in the ambient air on a substrate, a radiation source for irradiating the substrate, a detector for detecting an optical property of the particles deposited on the substrate, a Raman detector for detecting Raman-shifted radiation scattered by the particles deposited on the substrate, and a controller operably linked to the Raman detector, wherein said controller restricts detection of Raman-shifted radiation only to particles for which the optical property is characteristic of the pathogen.

33. The device of claim 32, wherein said-device is housed in a backpack.

34. The device of claim 32, further comprising a vapor sensor for continuous air monitoring.

35. The device of claim 32, wherein the air handling system further comprises a vapor sensor for continuous air monitoring.

* * * * *